United States Patent [19]

Shen et al.

[11] Patent Number: 5,029,082
[45] Date of Patent: Jul. 2, 1991

[54] CORRELATIVE ANALYSIS IN MULTI-DOMAIN PROCESSING OF CARDIAC SIGNALS

[75] Inventors: Xiguang Shen, North Point; Genquan Feng, Beijing; Ruan Lian, Beijing; Changqing Wang, Beijing; Jing Lian, Shenzhen; Chi Liu; Shizhong Lai, both of Guangzhou; Jilin Yang, Shenzhen; Qinwei Yiu; Gunagqi Zhang, Shenzhen; Peixin Feng; Yiexun Xia, both of Tianjin; Baohuai Li, Shenzhen; Lijun Cai, Shenzhen; Jianping Su, Shenzhen; Shi Zheng, Shenzhen, all of China

[73] Assignees: Wide Trade Foundation Ltd. & Export Corporation, Hong Kong; China Xiao Feng Technology & Equipment Co., Beijing; China National Electronics Import, Guangzhou, all of China

[21] Appl. No.: 474,246

[22] Filed: Feb. 5, 1990

Related U.S. Application Data

[63] Continuation of Ser. No. 99,892, Sep. 22, 1987, abandoned.

[30] Foreign Application Priority Data

Mar. 30, 1987 [CN] China ................................ 87102381

[51] Int. Cl.$^5$ ........................................... A61B 5/0402
[52] U.S. Cl. ................................. 364/413.06; 128/699
[58] Field of Search ............................... 128/699, 731; 364/413.05, 413.06

[56] References Cited

U.S. PATENT DOCUMENTS

| | | | |
|---|---|---|---|
| 4,201,224 | 5/1980 | John | 128/731 |
| 4,216,780 | 8/1980 | Rubel et al. | 128/699 |
| 4,305,400 | 12/1981 | Logan | 128/670 |
| 4,421,122 | 12/1983 | Duffy | 128/731 |
| 4,422,458 | 12/1983 | Kravath | 128/671 |
| 4,428,381 | 1/1984 | Hepp | 128/715 |
| 4,680,708 | 7/1987 | Ambos et al. | 364/417 |
| 4,697,597 | 10/1987 | Sanz et al. | 128/699 |
| 4,700,712 | 10/1987 | Schmid | 128/699 |
| 4,732,158 | 3/1988 | Sadeh | 364/417 X |
| 4,736,751 | 4/1988 | Gevins et al. | 128/731 X |
| 4,757,824 | 7/1988 | Chaumet | 128/716 |

OTHER PUBLICATIONS

Vinke, R. V. H. et al., "Implementation and clinical evaluation of computer-assisted analysis of exercise ECGs", Conference: Computers in Cardiology, Rotterdam, Netherlands, Sep.-Oct. 1977, 345-54.

Chatterjee, P. C. et al., "A simple VCG system with temporal dimension, directional reference and display of component loops", *J. Biomed. Eng.*, vol. 4, No. 2, Apr. 1982, 149-52.

BEAM brochure, Braintech, Inc., date unknown.

*Primary Examiner*—Clark A. Jablon

[57] ABSTRACT

An apparatus and method for detecting and processing bioelectric signals, such as ECG, VCG, EEG, etc, comprising: a plurality of electrodes for detecting electric signals from different locations on a human or animal body; a signal collecting device for synchroneously collecting multi-channel signals via the electrodes; a signal processing device for performing time domain, frequence domain and space domain processing on the collected signals; and a signal output device including a CRT and a graphic printer. In addition, the apparatus further comprising an external memory, a keyboard and an alarming device. By using the apparatus and method of the present invention, the examination of heart brain and other organs may be performed simultaneously by way of synchronized sampling multi-domain processing, curves and parameters tables displaying an automatic judgement, thereby accomplishing a quick detection and processing of the bioelectric signals.

16 Claims, 16 Drawing Sheets

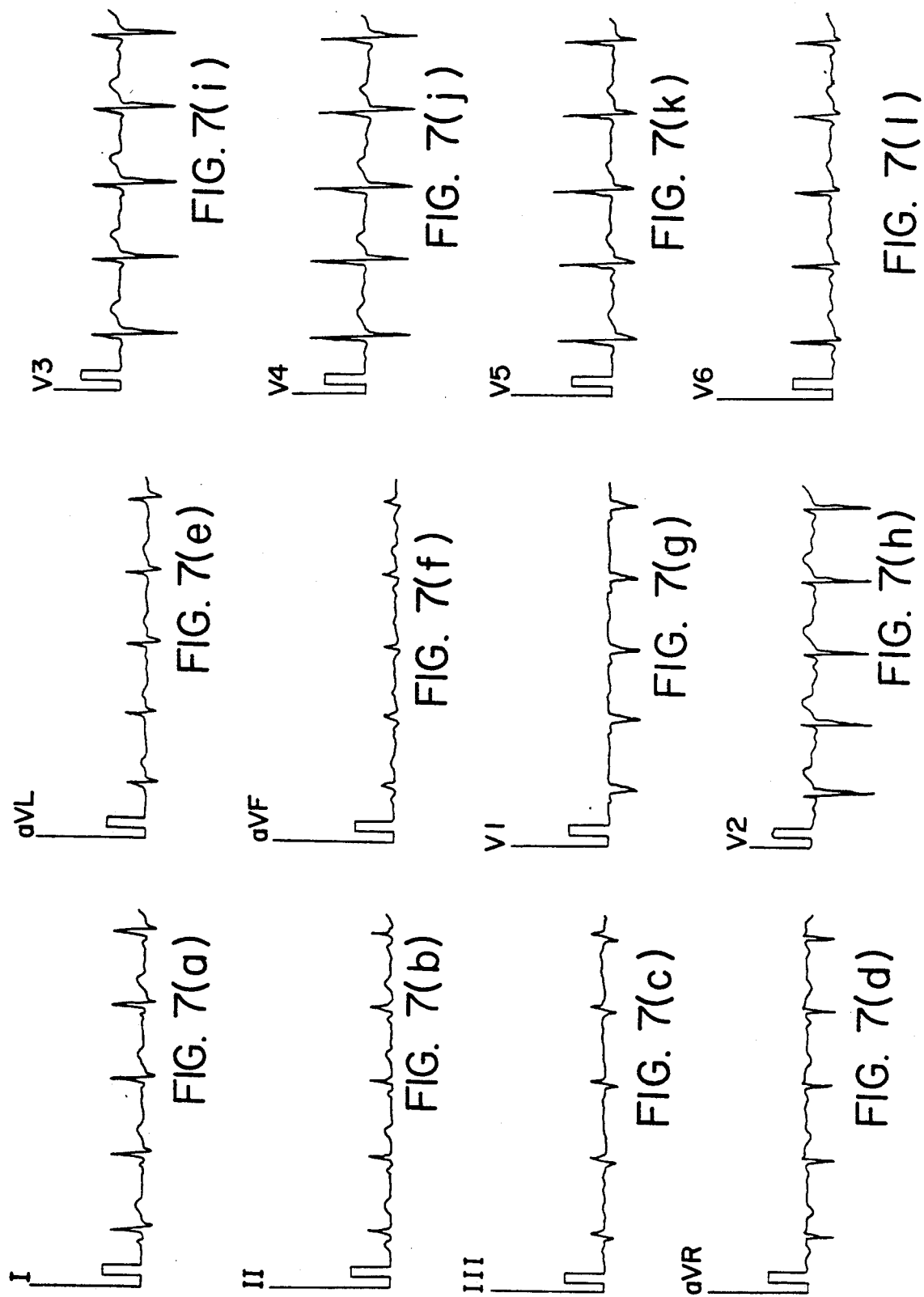

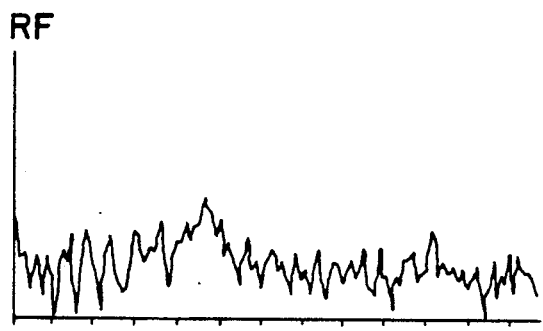
FIG. II(a)
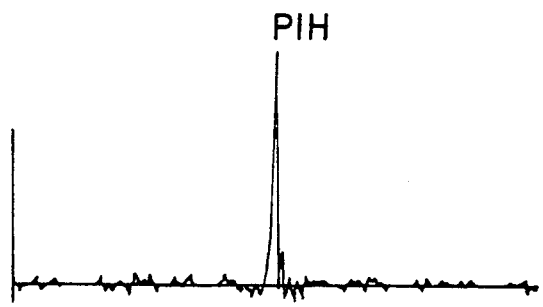
FIG. II(d)
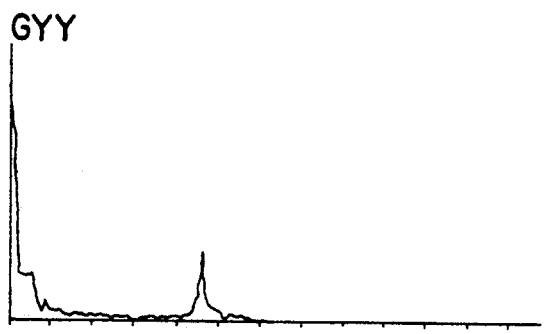
FIG. II(b)
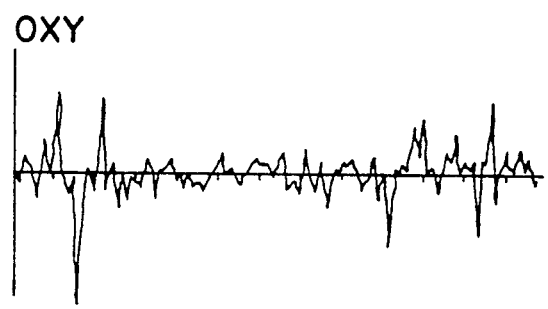
FIG. II(e)
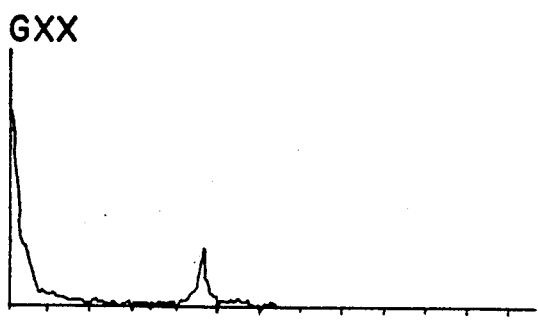
FIG. II(c)
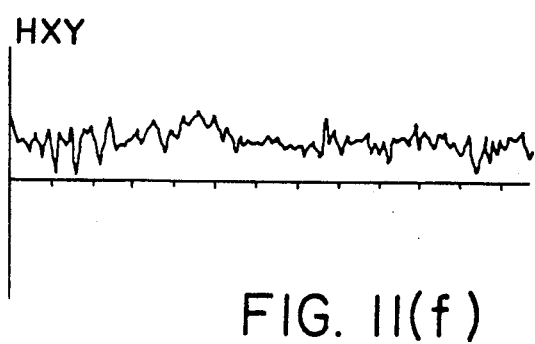
FIG. II(f)

CORRELATIVE ANALYSIS IN MULTI-DOMAIN PROCESSING OF CARDIAC SIGNALS

This application is a continuation of application Ser. No. 07/099,892 filed on Sept. 22, 1987, now abandoned.

FIELD OF THE INVENTION

The present invention relates to an apparatus and method for detecting and processing bioelectric signals and, more particularly, to an apparatus and method which are used to detect synchronously, via a plurality of detecting electrodes, multichannel electric signals relevant to the electrophysiological activities of certain human and animals' organs, such as the heart, brain or the like, and to perform analysis in the time domain, space domain as well as in the frequency domain to obtain vital information corresponding to the status of the organs, thereby to and the diagnosis of diseases and evaluation of health.

DESCRIPTION OF THE PRIOR ART

In the prior art, different techniques for detecting and processing bioelectric signals, such as electroencephalography (EEG), electrocardiography ECG, vectorcardiography (VCG), etc, have been developed based on achievements of electrophysiological researches on humans and animals. These techniques have progressed significantly with the combination of modern electronics and computer technology.

Recently, a MAC 12 automatic electrocardiogram system manufactured by Marquette Electronics Inc. Wisconsin, USA has been commercially available. This device is used to detect simultaneously on 12 Wilson's leads and produce a display of all 12 leads arranged on one single page. With information processing techniques and corresponding software, this ECG system can perform automatic ECG analysis in time domain, including ECG measurement, waveform identification and rhythm analysis. It is also capable of pacemaker evaluation, full disclosure Holter documentation and stress test monitoring with a treadmill. The system's data and report may be presented on a crystal liquid display and stored on diskettes.

A 3 lead vectorcardiogram system (model VA-3GR), manufactured by FUTEK corp. Japan, has recently been commercially available which is used to detect simultaneously on 3 Frank's leads. The signals thus detected are converted to digital form and stored in a memory for later recall of the stored data. The stored digital data is processed through a D/A converter to form analog data and X-Y grapher or displayed on a CRT as VCG loops.

In addition to the above, other progresses have been utilized in EEG detecting and processing techniques.

Since in all these ECG, VCG and EEG detecting and processing techniques, operation was confined to only one certain organ (heart or brain) and limited to only one lead system, such as the Wilson's leads system, Frank's leads system or brain leads system, consequently, some problems permanently difficult to solve.

First, in the prior art, the identification of ECG, VCG and EEG waveforms and diagnosis made thereby, no matter whether it is manual or automatic, are only performed individually in time domain or in space domain, these single domain operations can not overcome the defects inherent in these detecting techniques. For example, ECG is not sensitive to some diseases, while VCG is not useful for problems such as arrhythmia. Therefore, it is difficult to further improve the detection and diagnosis of heart and brain diseases.

Second, when different detecting techniques are applied to the same subject for making a correlated analysis, the detection and diagnosis are restricted by the prior art approaches since ECG, VCG and EEG are usually detected respectively by different equipment at different times and places. All these factors make the whole examination procedure complex and burdensome to the patients, especially those having serious heart or brain problems because the diagnosis and treatment should be quickly finalized, and in such cases the restrictions of the prior art are obvious.

It must be pointed out that when the examinations are performed one by one in the abovementioned way, the information obtained at different times by respective equipments are not well correlated with each other. Since the abnormal signals of ECG, VCG and EEG occur irregularly, especially the capture of some abnormal signals which are of pathological importance and are quite random, such as ventricular premature contraction signal of ECG. Therefore, it is difficult to detect the same abnormal signal on different leads at different times by using the prior art equipments. Apart from abnormal signals, signals detected individually on different leads at different times lack correlation and comparability since the status of the examined organs changes from time to time, so it is hard to make a comprehensive diagnosis based on the information obtained thereby.

Furthermore, when diagnosing diseases based on single domain analysis, since there are differences between bioelectric signals detected from different individuals or detected from the one individual but not in the same status, also there are errors in instrumentation and calculations, so reliable diagnoses are very hard to make for many diseases whose detected data are within a ambiguous range; therefore, the diagnosing effects of these techniques are restricted.

To sum up, owing to the restrictions of the prior art techniques, the ECG, VCG and EEG can not form an organic integrality for detecting and processing bioelectric signals, and are thus unable to accomplish a multidomain dynamic correlative analysis of the bioelectric signals detected from different organs.

SUMMARY OF THE INVENTION

According to the principles of theory of control, information theory and systematic engineering a human body can be considered as an integral big system which communicates physiologically and psychologically with the external environment through different approaches, so the health of a human body is influenced by many internal and external factors. For a human body, the heart and brain are two closely related, yet to some extent relatively independent, sub-systems. Their healthy status are also subjected to many internal and external factors. It is determined by the complicated effects of the internal and external environmental factors for the multiplicity and complexity of the detection and diagnsis of heart and brain diseases. There is no single way of detecting and processing which can completely reveal the complicated principles of the heart and brain diseases. Different kinds of information for the internal characteristics of these two sub-systems can be obtained by applying a plurality of electrodes on different locations of a human body and detecting electric signals therefrom. During a period of time when the states of the heart and brain, as the sources of information, are relatively stable, if the bioelectric signals are detected and processed by a single approach, no matter from which leads system these signals are obtained, and no matter in which domain, such as time domain, frequency domain, space domain or any other domain, the results analysed are only part of the characteristics of these information sources and only reveal one respect of them.

Much more comprehensive information about the characteristics of these information sources can be obtained only by simultaneously detecting electric signals from different organs through several leads systems and performing multi-domain analysis, researches of dynamic process and synthetic evaluations of the detected signals. In order to ensure the identity of the information sources during this comprehensive detecting and analysing process, namely to guarantee the dynamic correlation and comparability within the detected signals, it is of key importance to detect the electric signals synchronously through different leads system on different organs for successfully obtaining the information. The multi-domain analysis thus developed must be performed on the basis of a set of pathological criteria which are set up according to medical statistic methods and depending on a large-scale collection of multi-domain electric signals detected from patients with heart and brain diseases having been definitely diagnosed by medical experts. From these detected signals, the characteristic parameters are derived from each domain and then compared, analysed and classified according to statistic methods so as to determine the pathological criteria for the multi-domain synthetic analysis, the ambiguous range of each criterion and their meaning in clinical use, thereby to establish a basis for automatic diagnosis of different diseases.

Based on the above conceptions, the present invention provides an apparatus and method for synchronously detecting and correlatively analyzing the cardiac and encephalic electric signals from different leads systems of the prior art. According to the apparatus and method of the present invention, multi-channel electric signals corresponding to the electrophysiological process of the heart, brain and other vital organs are synchronously detected through a plurality of electrodes applied to different locations on a human or animal body, and correlative analysis is performed on each channel of electric signals in time domain, frequency domain, and space domain so as to make the multi-factor comparison, comprehensive evaluation and dynamic tracing according to the correlations between the different channels of signals and the complementary effects of the analysis made in different domains, thereby increasing the accuracy and reliability of the diagnosis. With the apparatus of the present invention, the detected and processed results can be displayed on a monitor or a graphic printer for clinical us by medical staffs, thus the examination procedure is significantly simplified for the convenience of both doctors and patients, especially in those urgent cases when time is crucial in saving lifes. Finally, the processed results can be compared with the above-mentioned pathological criteria for multi-domain correlative analysis obtained from medical statistics of clinical data, so as to make an automatic diagnosis for many diseases and an alarm according to the results of the diagnosis can be developed to alert and notify the operator in case the patient is in danger.

One objective of the present invention is to provide a detecting apparatus which can detect synchronously multi-channel bioelectric signals through different leads systems on different organs.

Another objective of the present invention is to provide an apparatus which can perform multi-domain processing on the multi-channel synchronous bioelectric signals in time domain, frequency domain and space domain.

Yet another objective of the present invention is to provide an apparatus which can perform automatic waveform identification of different parameters for the output after the multi-domain processing.

Yet another objective of the present invention is to provide an apparatus which can perform comparison and evaluation of various parameters to fulfill the automatic diagnosis of diseases.

Yet another objective of the present invention is to provide an apparatus which can provide simultaneously or respectively the output of the waveform of the multi-channel synchronous signals, their characteristic parameters and evaluation results.

Yet another objective of the present invention is to provide a detecting and processing method related to the above-mentioned apparatus.

According to the present invention, a preferred embodiment of the apparatus for detecting and processing bioelectric signals comprises:

a plurality of detecting electrodes for detecting simultaneously multi-channel electric signals from different locations on a human or animal body, which can be any conventional ECG and EEG electrodes in prior art;

an electric signal collecting device connected to the detecting electrodes for combining, amplifying and A/D converting the electric signals detected by the electrodes and then synchronously sampling and storing these dynamically changing signals;

a signal processing device adopted for performing multi-domain process, waveform identification, disease diagnosis and classification based on the data stored in the signal collecting device; and a signal output device for displaying simultaneously or respectively the waveform curves, characteristic parameters and diagnostic results of the detected signals processed by the signal processing device.

In addition, the preferred embodiment of the apparatus for detecting and processing bioelectric signals further comprises:

a keyboard for inputting into the signal processing device information about the patients and operating instructions, and for performing manual adjustment of the waveform identification during processing procedure;

an external memory device for storing processed signals and information fed in through the keyboard about the patient's name, sex, age, etc, to facilitate the tracing of the development of disease and statistical analysis; and an alarm device for alerting and notifying the operator of all dangerous cases according to the classification of the disease based on the processed signals.

According to the present invention, a preferred embodiment of the method for detecting and processing bioelectric signals comprises the following steps:

a) detecting simultaneously electric signals through a plurality of detecting electrodes applied to various locations for different organs of a human or animal body;

b) amplifying the detected multi-channel signals by a multi-channel amplifier with parallel analogue output;

c) converting the amplified multi-channel parallel analogue output into multi-channel digital signals by a multi-channel A/D converter;

d) sampling synchronously the multi-channel digital signals at a predetermined frequency by a sampling circuit;

e) storing the sampled signals into a buffer;

f) fetching data from the buffer by a signal processing device, and then performing time-domain analysis on the data of each channel respectively, frequency-domain analysis on the data of any two channels, and space-domain analysis on the data of predetermined three channels, to obtain the corresponding time-domain, frequency-domain and space-domain waveform curve; and g) providing the curves displayed by an output device.

In addition, the preferred embodiment of the method for detecting and processing bioelectric signals further comprises the following steps:

h) identifying the waveform of each curve by the signal processing device and for some hard-to-identity waveforms performing manual adjustment of this identification through a program to obtain a parameter table for each curve, to be transferred to the output device;

i) comparing and evaluating the parameters of each table with a set of pathological criteria for multi-domain correlative analysis by its signal processing device to determine the kind of disease, then providing the determined results to the output device;

j) classifying the determined results according to its seriousness by the signal processing device and initiating an alarming procedure if a dangerous case is present; and k) alerting and notifying the operator through an alarming device.

The bioelectric signal detecting techniques, such as ECG, VCG, EEG, etc which are independent to each other in prior art, have been combined to form a unified comprehensive detecting and processing technique through the apparatus and method of the present invention. Larger quantity as well as better quality of the information obtained from a living body have been achieved by this unified detecting and processing technique. For example, while doing ECG detection, EEG is obtained at the same time and correlative analysis is made to the combination of these two. In this way, it is possible to avoid psychological interferences in the ECG reading. On the other hand, while doing EEG detection, ECG is obtained at the same time and correlative analysis is made to the combination of them, so it helps to overcome the noise developed in EEG signal by ECG and the pulses of the brain artery. The mutual relations and influences between different organs can be understood at a more comprehensive level by using a unified approach to detect the electrophysiological activities of several organs, and thereby the diagnosis can be made more reliable.

With the utilization of the apparatus and method for detecting and processing bioelectric signals according to the present invention, the medical staffs and researchers may hereafter obtain useful information which was impossible in prior art, from the detected results, such as curves of energy spectrum, autocorrelative function, cross-correlative function, coherent function, transfer function, pulse response function, etc. of both the ECG and EEG signals, all these curves reflecting characteristics of the electrophysiological activities of the heart and brain. The frequency-domain detecting technique, fulfilled and developed by the present invention, realizes for the first time in the medical science the automatic identification and diagnosis of the heart and brain electric signals based on their frequency features, and has developed from the experimental lab stage to widely clinical practices.

The frequency domain detector technique is further facilitated by the apparatus and method of the present invention the synchronized or subsynchronized sampling of multi-channel signals, so the data collected thereby are highly correlated and regularized, and suitable for mutual verification and comparison. In addition, the synchronized detection performed to the dynamic activities of different organs is beneficial in observing the development of diseases, making the device of the present invention much more valuable in clinical practices.

The accuracy of the diagnosis of heart and brain diseases is significantly improved by the multi-domain analysis achieved by the apparatus and method of the present invention, especially when the detected values are within their ambiguous ranges, thus diseases at their early stage can be decisively diagnosed by the multi-domain correlative analysis made on these ambiguous values. It has been proved by clinical experiments that the multi-domain correlative analysis improves the sensitivity of diagnosis, and the accuracy and reliability of diagnosis are distinctively better than any single-domain analysis.

The special design of the hardware and software of the present invention accomplishes not only the automatic identification of the waveforms in each domain, but allows manual adjustment of the waveform identifications performed on some hard-to-identify waveforms by an operator according to practical needs. This is very helpful in improving the accuracy and reliability for some difficult-to-diagnose cases.

The apparatus and method of the present invention accomplishes synchronized collecting, high-speed processing and automatic analysing of the multi-domain information, and its output includes curves, parameter tables etc. The total procedure of detection and processing (from the start of operation to the end of printing) takes abort 10 minutes and this is quite beneficial in urgent cases.

The apparatus of the present invention is small and light-weight, and works well in different environments. It can be assembled in a portable or cart form, so it is convenient for doctors to move and operate it everywhere or carry it on patient visits. By adopting conventioned AC/DC techniques, the apparatus can be used in various ambulatory circumstances, health check and field researches.

The apparatus and method of the present invention can be used not only for detecting ECG, VCG and EEG, but also for electromyogram, skin potential and other multi-domain detections on human or animal bodies by adopting different electrodes, amplifier modules, and corresponding programs, so as to share the expensive hardware and software resources.

In summary, the apparatus and method of the present invention have provided a reliable and highly automatic new approach for diagnosing and differentiating diseases, observering therapeutic effects, monitoring the conditions of those seriously ill patients and performing biological research. The outstanding performances of the present invention have been shown in clinical and laboratory tests.

The above-mentioned and other objectives, features and advantages of the present invention will become more apparent in the following detailed descriptions of the preferred embodiments of the invention together with the accompanying drawings.

BRIEF DESCRIPTION OF THE DRAWINGS

FIGS. 7a-i show the waveforms of ECG time domain processed signals;

FIGS. 11a-f show the waveforms of EEG frequency processed domain processed signals;

DETAILED DESCRIPTION OF THE INVENTION

Figure 1:
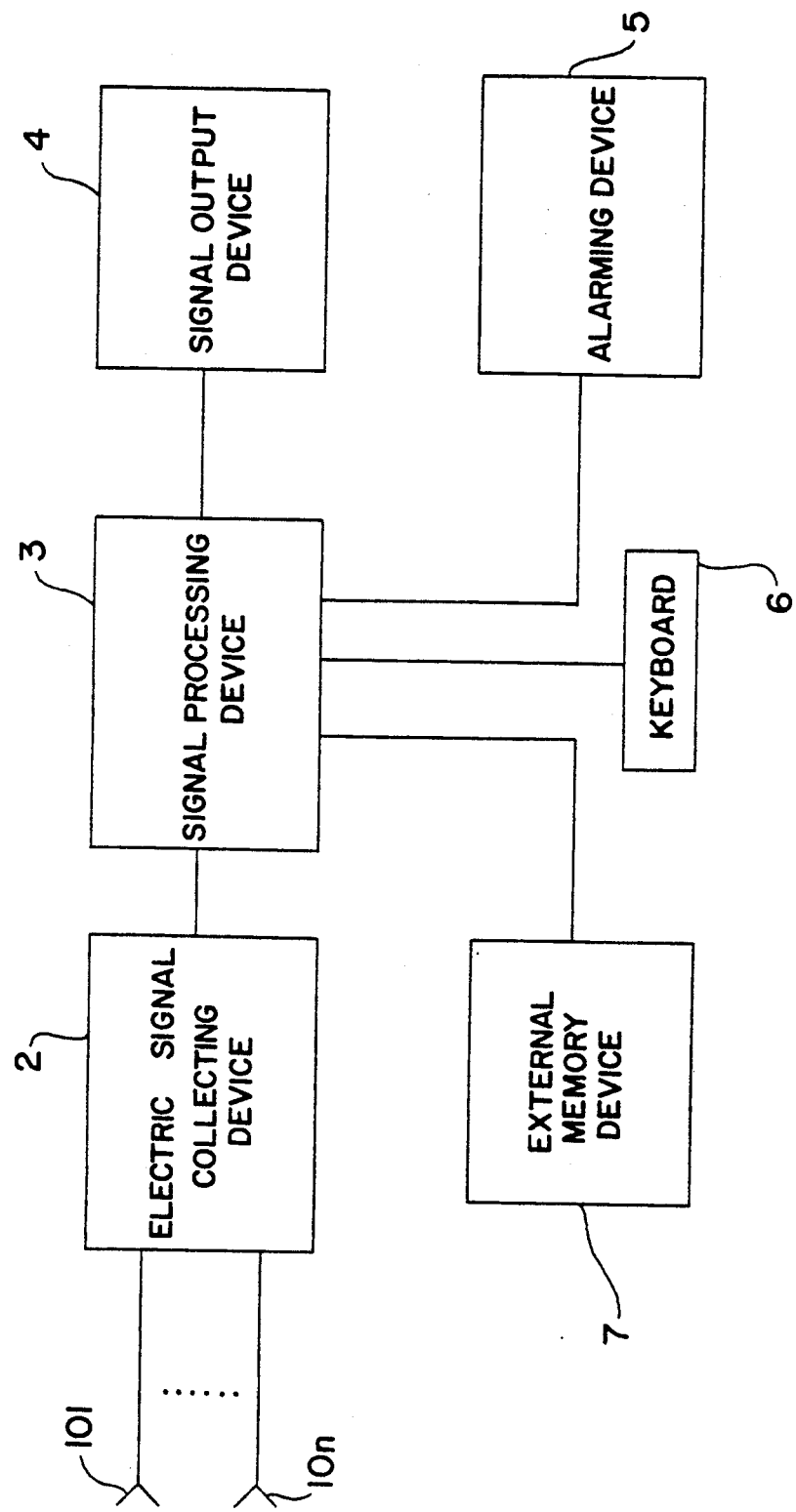
FIG. 1 is an illustrative block diagram of the apparatus for detecting and processing bioelectric signals of the present invention.

Referring to FIG. 1, there is shown an illustrative block diagram of the apparatus for detecting and processing bioelectric signals according to the present invention. In FIG. 1, numeral 101-10n denote n electrodes. Their total number n can be selected according to clinical needs. An electric signal collecting device 2 is shown in detail in three different embodiments in FIGS. 2 to 4. A signal processing device 3 is shown in detail in two embodiments in FIGS. 5 and 6. Numeral 4 indicates a signal output device and numeral 5 indicates an alarm device which may be any kind of audio or video device, or their combination, and which can also be combined with the signal output device 4 as part of its output in the form of indicating characters. Numeral 6 indicates a keyboard by which the operator controls the operation of the whole apparatus and inputs the information about the subject, such as name, sex, age, case number, date of examination, etc. The waveform identification procedure of the signal processing device 3 can be manually adjusted through the keyboard 6. Obviously, the keyboard 6 may be replaced by any other input device. Numeral 7 indicates an external memory device of any conventional type for storing detected multi-channel signals and the information about the subject so that the cases may be accumulated for a later data processing and future medical statistical use.

Figure 2:
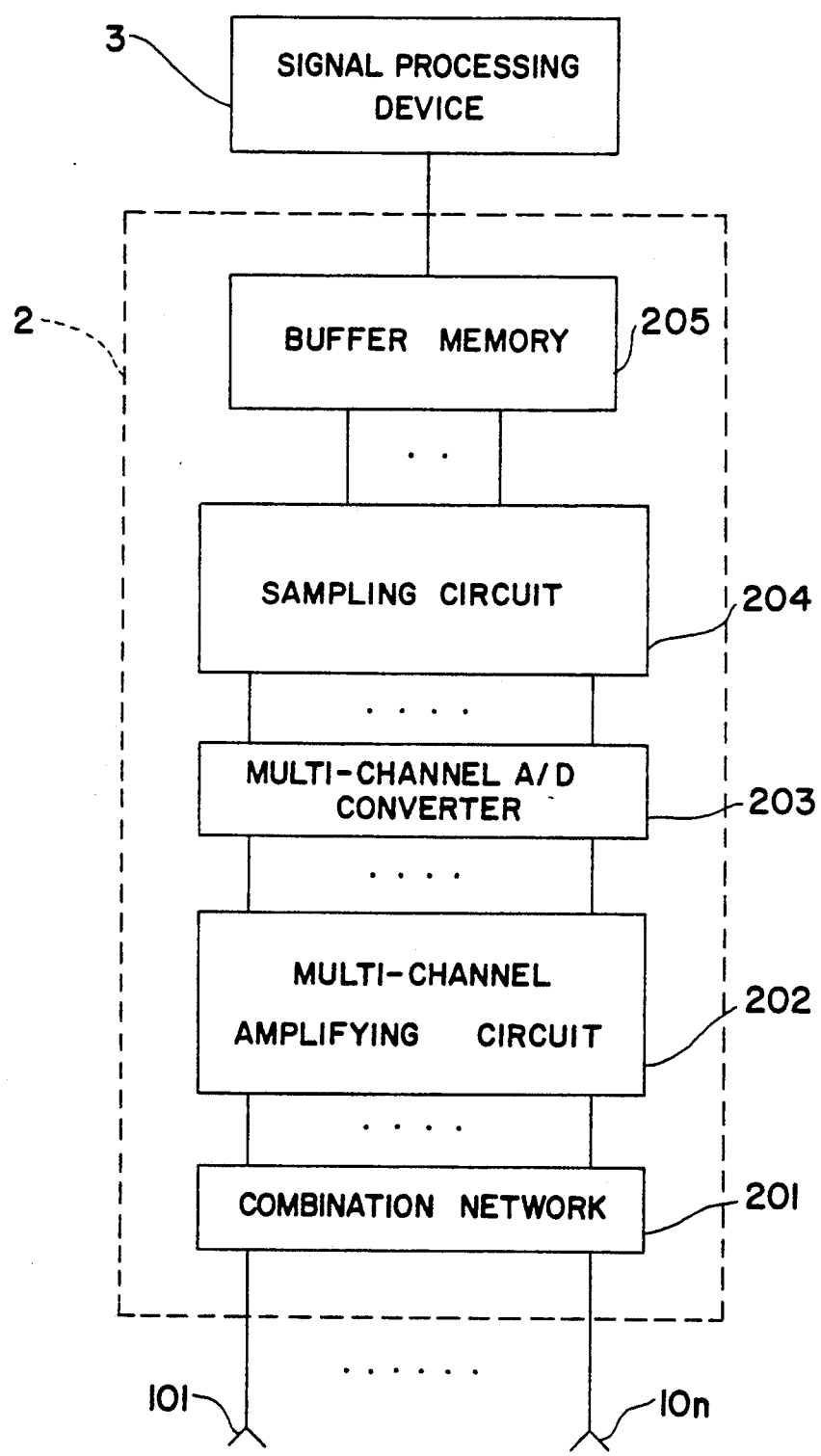
FIG. 2 is an illustrative block diagram showing a first embodiment of the electric signal collecting device 2 shown in FIG. 1.

Referring to FIG. 2, there is shown a block diagram illustrating an embodiment of the electric signal collecting apparatus 2 shown in FIG. 1. In FIG. 2, a combination network 201 has inputs connected to the detecting electrodes 101 to 10n for detecting simultaneously electric signals from different locations on a human or animal body, and multi-channel parallel outputs connected to a multi-channel amplifying circuit 202. The combination network 201 may be any conventional type used for ECG or EEG, or their combinations so as to provide output signals in conformity with the leads systems using international standards, such as Frank leads system, Wilson leads system, etc. Each channel of the multi-channel amplifying circuit 202 is connected to one of the outputs of the combination network 201 and the gain of each channel is predetermined according to different requirements. The output of each channel of the circuit 202 is connected to a corresponding input of a multi-channel A/D converter 203 whose multi-channel parallel outputs are sampled synchronously by a sampling circuit 204. The sampled data are then stored into a buffer memory 205 for later processing by the signal processing device 3. From the embodiment of the electric signal collecting device 2 shown in FIG. 2, it is understood that the synchronized sampling performed by the sampling circuit 204 guarantees the bioelectric signals detected via electrodes 101 to 10n are stored in the buffer 205 in a synchronized format, so the multi-domain processing and correlative analysing between the channels of signals are performed thereafter on synchronized data and the detected signals of each channel will be able to reflect the dynamic processes of each of the vital organs.

Figure 3:
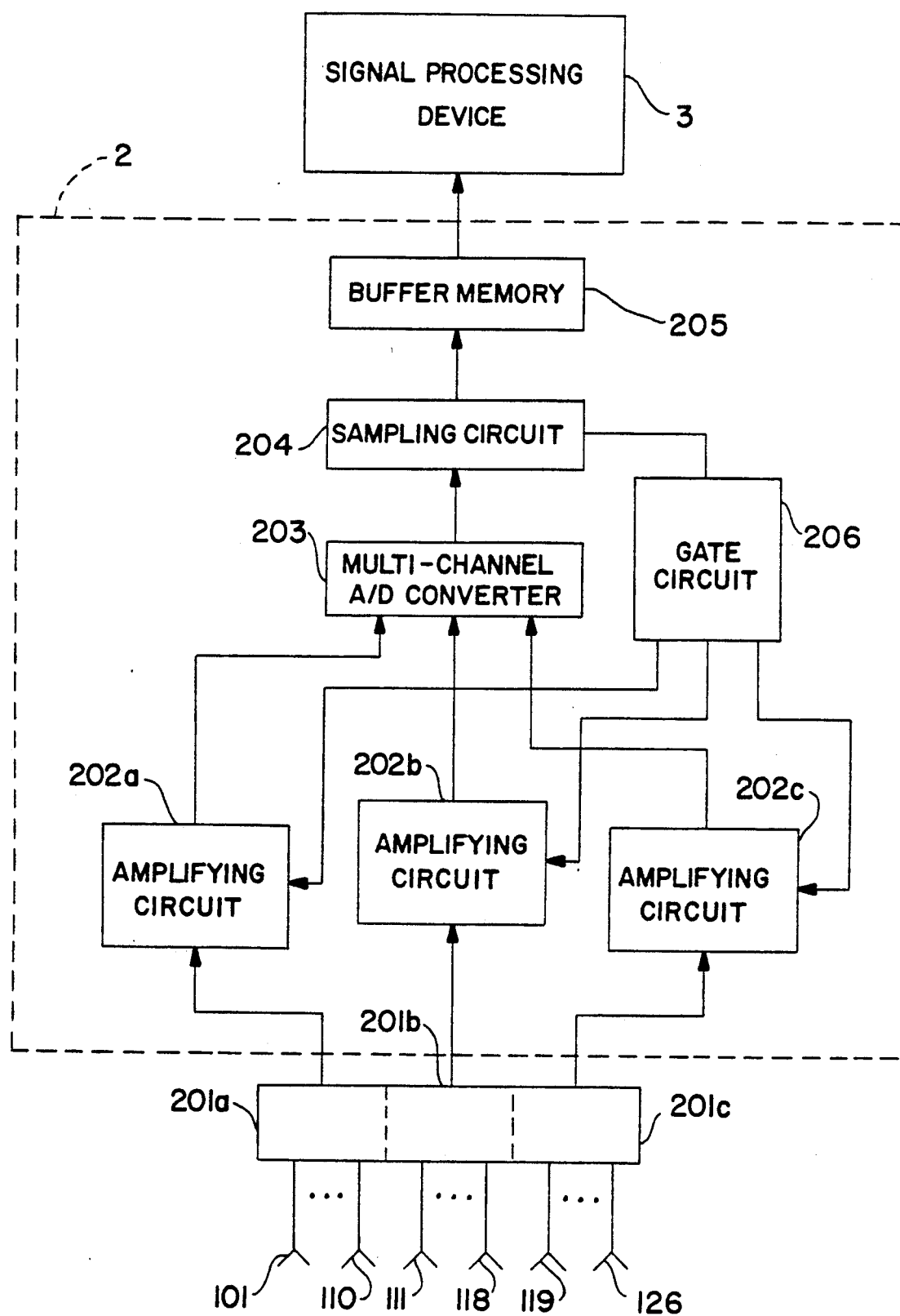
FIG. 3 is an illustrative block diagram showing a second embodiment of the electric signal collecting device 2 shown in FIG. 1.

Referring to FIG. 3, there is shown another embodiment of the electric signal collecting device 2 shown in FIG. 1. In this embodiment, the combination network 201 is divided into three parts 201a, 201b and 201c for ECG, VCG and EEG detection which correspond to the Wilson leads system, Frank leads system and EEG leads system, respectively. The three networks are connected to 10, 8, and 8 electrodes, respectively, which may be any conventional ECG or EEG electrodes. Three multi-channel amplifying circuits 202a, 202b and 202c are connected respectively to three combination networks 201a, 201b and 201c, and each of amplifying circuits has a gain determined by the requirements of its leads system, wherein, for example the scaled voltage of the circuits 202a and 202b is 1 mV and that of 202c is 50 $\mu$V. In FIG. 3, the multi-channel A/D converter 203, sampling circuit 204 and buffer 205 are similar in structure and function to that shown in FIG. 2, so they will not be further described here. In FIG. 3, the multi-channel amplifying circuits 202a, 202b and 202c are under the control of a gate circuit 206, which in turn is controlled by the sampling circuit 204. When the electric signal collecting device 2 starts to work, the multi-channel amplifying circuit 202a is gated first to work by the gate circuit 206. When the sampling circuit 204 performs a sampling procedure for 120 seconds, it issues a control signal to the gate circuit 206 which then gates the multi-channel amplifying circuit 202b to work for 5 seconds of sampling, then the circuit 206 gates circuit 202c to work for 120 seconds of sampling. In this way, the sampling circuit 204 can perform synchronized sampling to the networks 201a, 201b and 201c, respectively. It is obvious that the number of combination networks and amplifying circuits is not limited to three, and each combination network is not restricted to a certain leads system, they can be recombined and extruded according to the requirements of clinical and laboratory practice. If these amplifying circuits and networks are recombined and extended, the gain and sampling time may be changed according to practical requirements to make a better observation of the dynamically varying process of the electric signals, so as to efficiently extend the functions and applications of the apparatus of the present invention and to share the expensive software and hardware resources.

Figure 4:
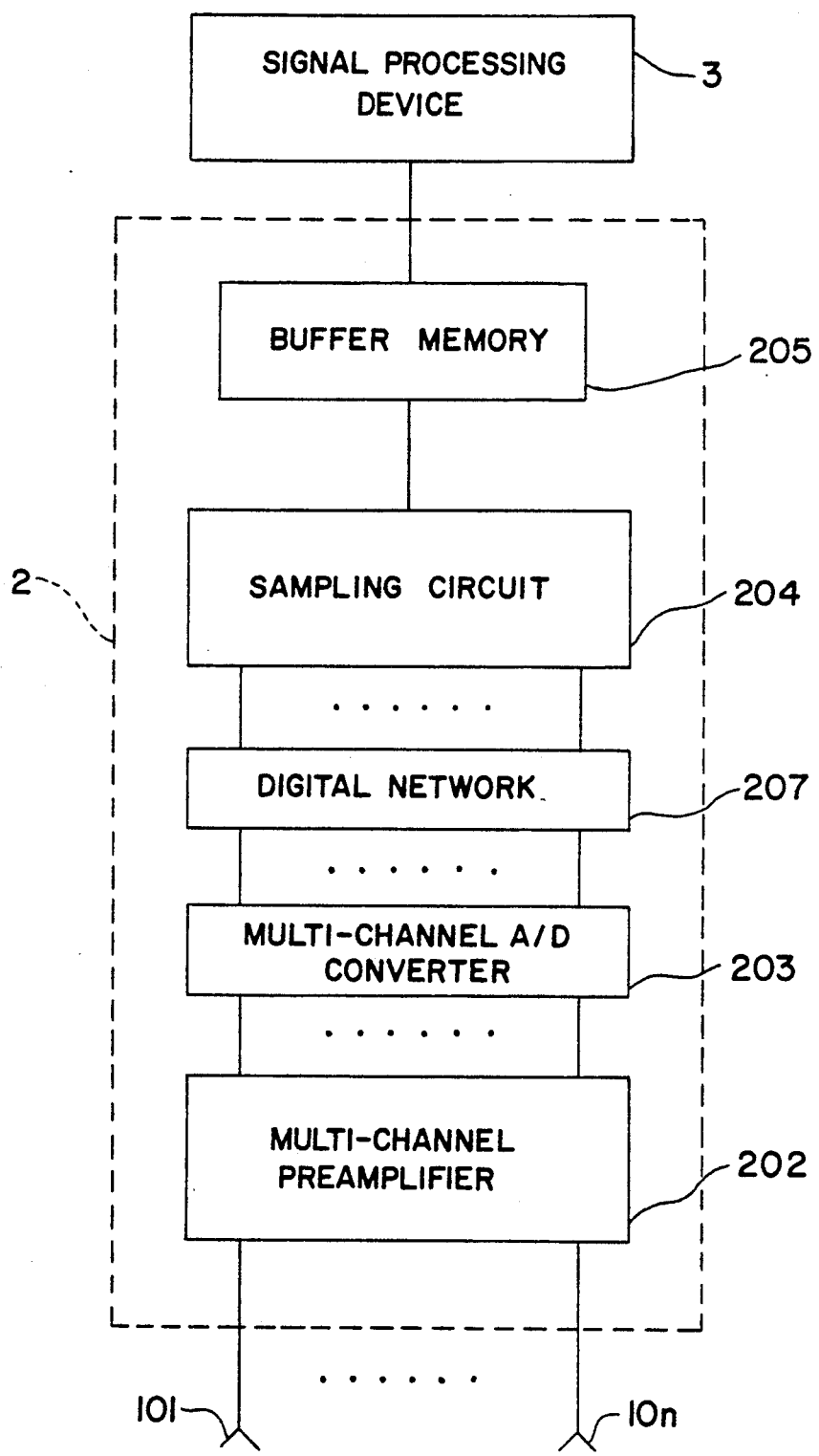
FIG. 4 is an illustrative block diagram showing a third embodiment of the electric signal collecting device 2 shown in FIG. 1.

Referring to FIG. 4, there is shown another embodiment of the electric signal collecting device 2. A multi-channel preamplifier 202 whose inputs are directly connected to a plurality of detecting electrodes is provided with outputs which are connected to a multi-channel A/D converter 203, further, the outputs of the converter 203 are connected to a sampling circuit 204 via a digital network 207 wherein a certain combination relationship between the input and output signals exists. As will be explained later, the same functions may also be accomplished by the software program in the signal processing device 3. In this way, the operator can change the combination relationship between the input and output signals by programming, and following this manner, the functions of the electric signal collecting device 2 may be expended easily to meet different clinical and laboratory needs, so as to adapt it to practical requirements in synchronized sampling on different leads systems or various organs.

Figure 5:
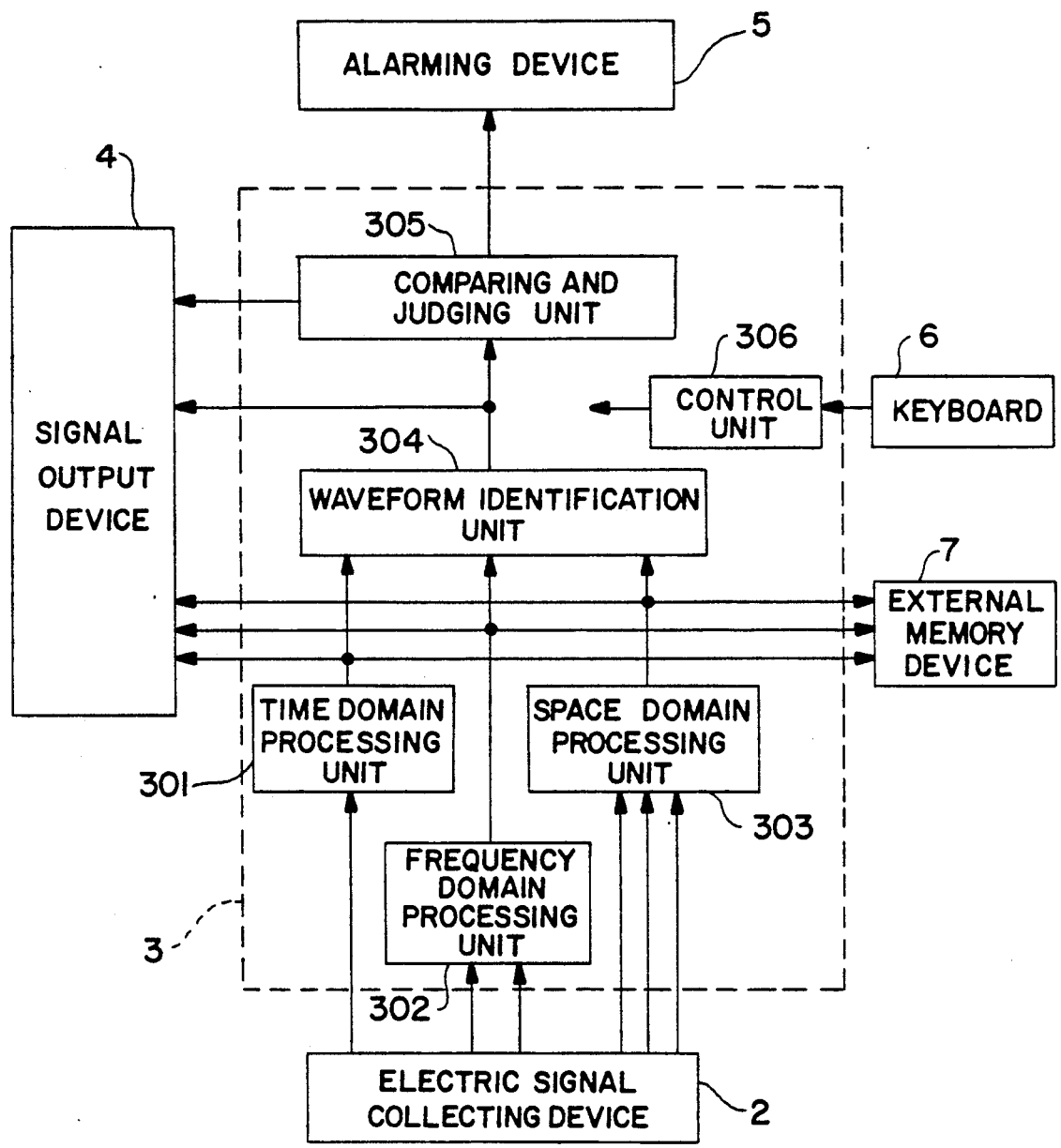
FIG. 5 is an illustrative block diagram showing an embodiment of the signal processing device 3 shown in FIG. 1.

Referring to FIG. 5, there is shown an embodiment of the signal processing device 3. Wherein the signal processing device 3 includes, a time domain processing unit 301, a frequency domain processing unit 302, a space domain processing unit 303, a waveform identification unit 304, a parameter comparing and judging unit 305 and a control unit 306. When the signal processing device 3 works, the above-mentioned three processing units 301, 302 and 303 fetch data respectively from the buffer 205 in the signal collecting device 2. The time domain processing unit 301 samples data at a required frequency (e.g. the sampling frequency of ECG is 250 Hz) and performs digital filtering and compressing, then provides its outputs to the output device 4 for graphing and printing and to the external memory device 7 for storing. The frequency domain processing unit 302 samples data in segments (each segment contains $2^n$ bits) for performing Fast Fourier Transform (FFT) at a predetermined sampling frequency (as for frequency spectrum of ECG and EEG, sampling frequency is normally selected within a range of 50-500 Hz). The FFT is performed on two corresponding channels of signals as functions X(t) and Y(t), respectively, and then their energy spectrum, autocorrelative function, cross-correlative function, transfer function, pulse response function, coherent function, etc, are computed The curves of these functions and their mathematical deductions are shown in FIGS. 8 and 11, and may refer to their descriptions later in this specification which are enough to disclose the present invention. They may also be found in *The Principles and Applications of Computer Analysis of ECG and EEG,* by Mr. Feng Gen-quan, who is one of the Inventors of the present invention, published in Chinese by Science Publishing House, in October of 1986. The contents of this book are incorporated herein. More specifically, in this book, there is a related summary on pages 126-127 wherein the below English translation is incorporated here as reference.

Since the visual justification method currently applied in clinical practice of ECG/EEG is confined to the signal and analysis in time-domain, effective or useful information is hard to extract. This difficulty in obtaining effective information lessens the effectiveness of diagnosis. From the point of view of ergonomics, we adopted the concept of Biocybernetics and regard the brain and heart, as special machines. Thus, we have successfully applied some common analytical procedures in engineering cybernetics such as power spectrum, transfer function, auto-correlation, pulse response, histogram and cross-correlation, etc., in the analysis of ECG/EEG signals through a computer. Theoretically this method has the following advantages:

(1) By using a visual justification method to analyze the ECG/EEG signals in time-domain, effective or useful information is hard to extract (such as the frequency components distribution, alteration of the waveforms, or the correspondence of deviations among cycles in different periods). also, it is hard to perform a precise, quantitative analysis. However, adoption of a frequency-domain analysis method (such as power spectrum and so on) allows the user to more clearly observe the characteristics of the information acquired, for example, to know at a glance, from the power spectrum chart, the power distribution among frequency components. Also, the chart shows the effects of alteration in waveforms and the corresponding deviations among cycles. Therefore, a quantitative analysis from these charts can be achieved.

(2) By using a visual justification method to analyze ECG/EEG signals in time-domain, it is very difficult to recognize the corresponding relationship of the waveform and frequency between the signals from two different leads, making it difficult to realize a quantitative analysis. However, using the correlative analysis in cybernetics, such as a transfer function, a coherent function, a cross-correlation or a pulse response, an user can effectively and quantitatively analyze the ECG and EEG signals and their corresponding relations in time difference, amplitude, frequency, and waveform between two leads. From these analyses, effective information can be obtained, thereby enhancing the success of the diagnosis.

(3) Since a computer is able to sample process data at high speed, it may sample and process large amounts of data corresponding to the ECG/EEG signals during a long sampling time period with precision data handling. Therefore, the computer analysis is based on a larger source of information, thereby allowing the extraction of more effective information both in quantity and accuracy than the conventional visual justification method of ECG and EEG. The operated results of these functions are provided to the output device 4 for plotting and to the external memory 7 for storing. The sampling frequency of the space domain processing unit 303 is determined as needed (it is between 250-1000 $H_z$ for VCG) and the unit 303 performs digital filtering on the three channels of signals, X, Y and Z, then the VCG loops on front plane (X,Y) horizontal plane (X,Z), left side plane (Y,Z) and their corresponding three-dimension cubic model is formed by selecting signal segments on three channels corresponding to P wave, QRS complex and T wave of ECG signal and provided to the output device 4 for plotting and external memory 7 for storing. In order to meet the requirements of the three processing units for different sampling frequencies, a basic sampling frequencies which is a multiple of each of three sampling frequencies has been selected (usually in the range of 500-2500 $H_z$ for multi-domain ECG) for the sampling circuit 204 in the electric signal collecting device 2. In this way, each of the three processing units may discretely fetch data from the buffer memory according to its own sampling frequency. The waveform identifying unit 304 of signal processing device 3 comprises three parts corresponding to three processing units 301, 302 and 303, respectively, each part performs waveform identification and position calculation on the outputs of its corresponding processing unit. During this process manual adjustment may be done if necessary, and in this way, three corresponding parameter tables are formed (references are made to curves in FIGS. 7–11 and flow chart in FIG. 12 and their relevant descriptions for the contents of the tables). The parameters of the three tables formed by the waveform identifying unit 304 are compared with predetermined pathological criteria for multi-domain correlative analysis by the parameter comparing and judging unit 305 in signal processing device 3, then judgement is made to the detected results based on the comparison and the final report is printed by the output device 4. Furthermore, the alarm device 5 may be instructed to alarm according to this judgement (refer to FIG. 13 and its relevant descriptions for more detail). The control unit 306 of the signal processing device 3 consists of a CPU which controls the operations of the signal processing device 3 as a whole with its different units operating at a certain clock frequency and time sequence The CPU is connected to the keyboard 6 for receiving input information about patients (such as name, sex, age, etc) and instructions, start and stop various operating procedures, and performing manual adjustments during waveform identification by the operator. Refer to FIG. 14 and its relevant descriptions for detail about the manual adjustment. In addition, the external memory 7 is capable of providing the device 3 with stored prior data about the patients for identification and processing.

Figure 6:
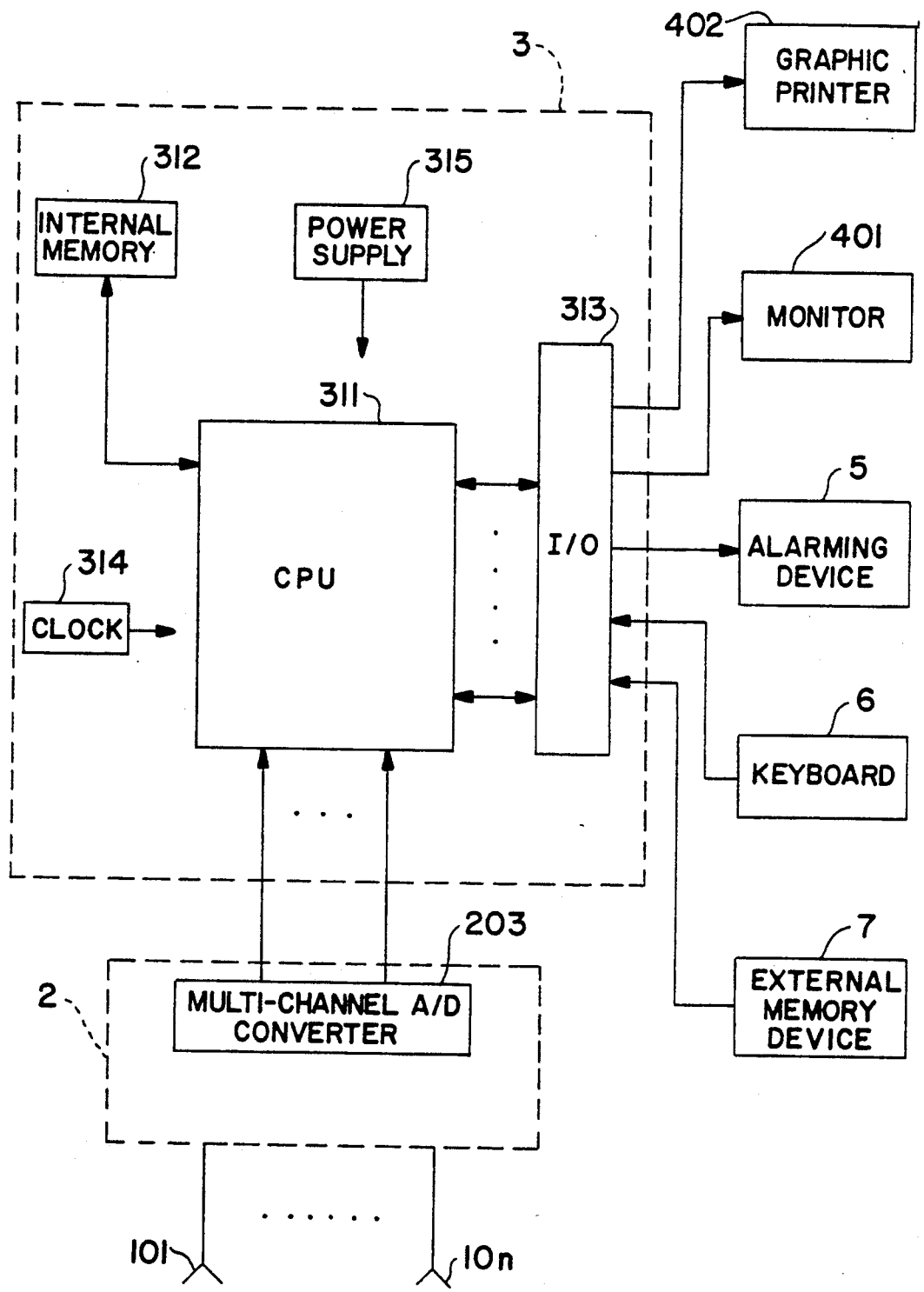
FIG. 6 is an illustrative block diogram showing another embodiment of the signal processing device 3 shown in FIG. 1.
Figure 8A:
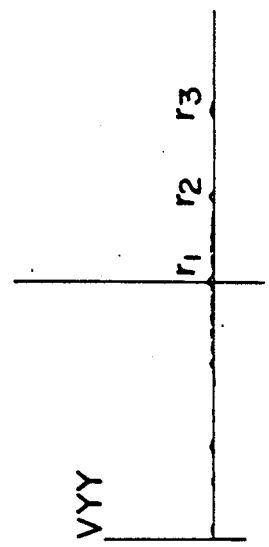
FIGS. 8a-i shows the waveforms of ECG frequency domain processed signals.
Figure 8D:
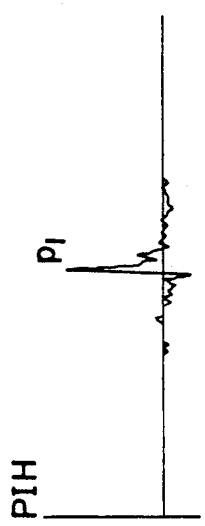
Figure 8G:
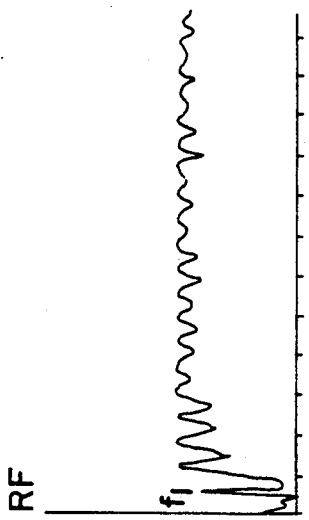
Figure 8B:
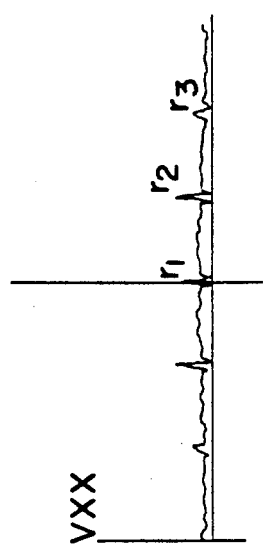
Figure 8E:
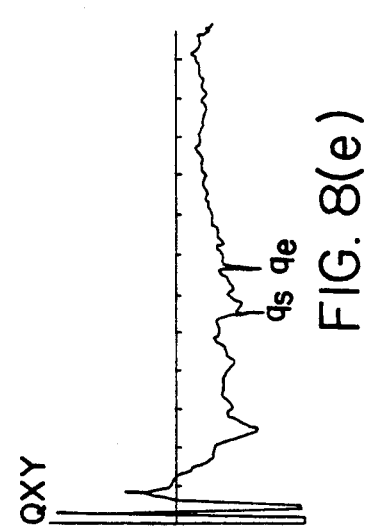
Figure 8H:
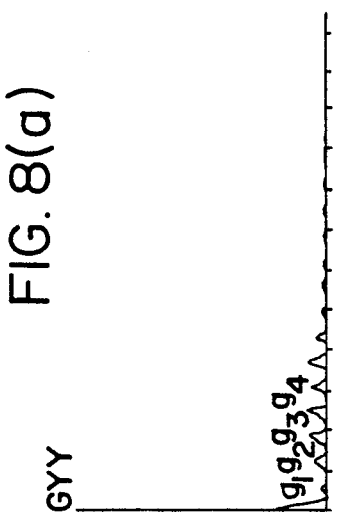
Figure 8C:
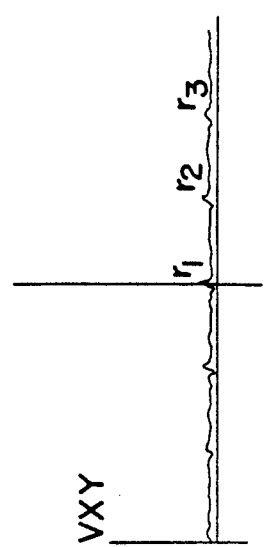
Figure 8F:
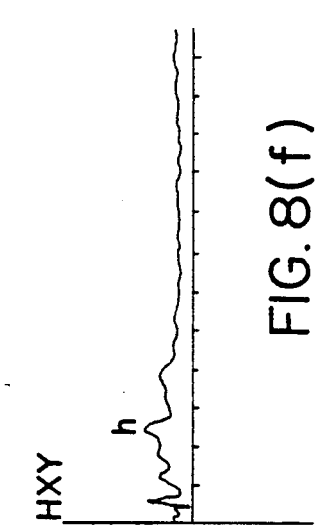
Figure 8I:
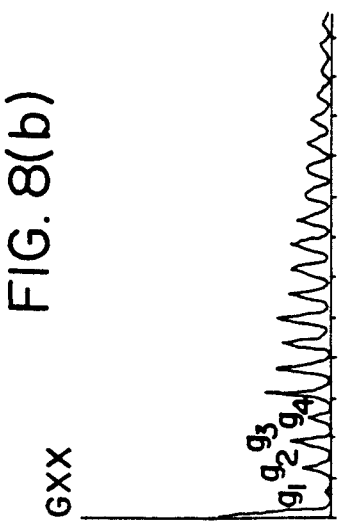
Figure 9A:
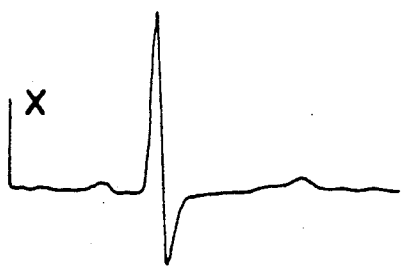
FIGS. 9a-f show the waveforms of ECG space domain processed signals.
Figure 9D:
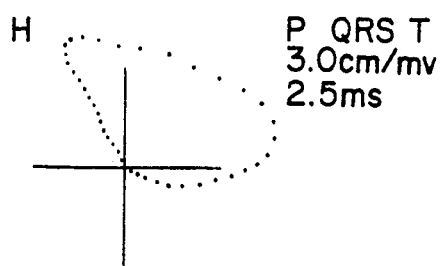
Figure 9B:
Figure 9E:
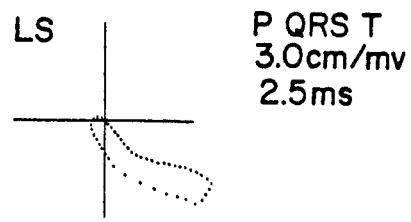
Figure 9C:
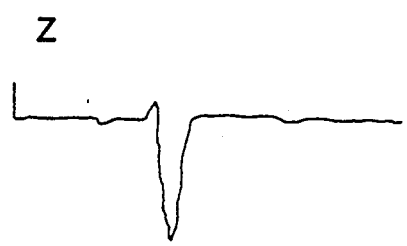
Figure 9F:
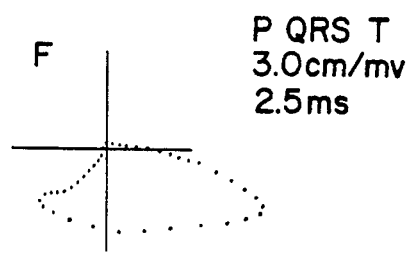

Referring to FIG. 6, there is shown another embodiment of the signal processing device 3. In FIG. 6, the signal processing device 3 comprises a CPU 311 which may be any 16-bits or more CPU, an internal memory 312 whose capacity exceeds 512k, an I/O interface 313, a clock circuit 314 and a power supply 315. In the embodiment shown in FIG. 6, functions of the units 301-306 shown in FIG. 5 are accomplished by CPU 311 in cooperation with corresponding software. It should be clarified that the functions of the sampling circuit 204, buffer memory 205 and digital network 207 in electric signal collecting device 2 shown in FIG. 4 may also be accomplished respectively by CPU 311 and internal memory 312 with software. The flow charts shown in FIGS. 12-16 and their relevant descriptions explain the principles of the software operations.

Referring to FIG. 7, there is shown the waveform of time domain signals of the output from the time domain processing unit 301 shown in FIG. 5. Curves of 12 leads of a conventional ECG signals are shown in FIG. 7.

In FIG. 8, there is shown the output waveforms of the frequency domain processing unit 302 shown in FIG. 5, wherein the curves are obtained by taking curves $V_5$ and II shown in FIG. 7 as functions X(t) and Y(t) respectively, and converting these waveforms from time domain to frequency domain by FFT. In the frequency domain processing of the present invention, the following equations are used:

$$F(w) = \int_{-\infty}^{+\infty} f(t) e^{-jwt} dt \quad (1)$$

FFT is performed on curves $V_5$ and II shown in FIG. 7, as X(t) and Y(t) respectively, to obtain frequency domain curves $F_x(w)$ and $F_y(w)$, and then the energy spectrum is obtained by equation:

$$G_{xx}(w) = F_x(w) \cdot F_x^*(w) \quad (2)$$

$$G_{yy}(w) = F_y(w) \cdot F_y^*(w) \quad (3)$$

so the energy spectrums $G_{xx}$ and $G_{yy}$ (shown in FIG. 8) are respectively derived from the curves $V_5$ and II shown in FIG. 7.

The cross-energy spectrum is obtained by equation:

$$G_{xy}(w) = F_x(w) \cdot F_y^*(w) \quad (4)$$

thus, the cross-energy spectrum $G_{xy}$ is derived from curves $V_5$ and II by frequency domain processing unit 302.

By equation of coherent function $$V_{xy}^2(w) = |G_{xy}(w)|^2 / G_{xx}(w) \cdot G_{yy}(w) \quad (5)$$

the coherent function curve RF shown in FIG. 8 is derived.

From equation $$H_{xy}(w) = \frac{Y(w)}{X(w)} = \frac{Y(w) X^*(w)}{X(w) X^*(w)} = \frac{G_{xy}(a)}{G_{xx}(a)} \quad (6)$$

the transfer function curves $H_{xy}$ and $Q_{xy}$ shown in FIG. 8 are derived by frequency domain processing unit 302. Wherein, $H_{xy}$ and $Q_{xy}$ are respectively the modulus and phase angle of the $H_{xy}(w)$, i.e.

$$H_{xy} = |H_{xy}(w)| = |G_{xy}(w)|/G_{xx}(w) \quad (7)$$

$$Q_{xy} = \tan^{-1} |tMAGX|/REALX \quad (8)$$

wherein $$X = G_{xy}(w)/G_{xx}(w) \quad (9)$$

The curve PIH shown in FIG. 8 is the pulse response function derived from the curves $V_5$ and II shown in FIG. 7 by frequency domain processing unit 302, this function is the inverse Fourier transform of the transfer function, i.e.

$$h(t) = F^{-1}[H(w)] \tag{10}$$

Derived by frequency domain processing unit 302 according to following equation:

$$R_x(\tau) = \int_{-\infty}^{+\infty} x(t)x^*(t+\tau)dt \tag{11}$$

The following equations are obtained:

$$R_x(\tau) = F^{-1}[G_{xx}(w)] \tag{12}$$

$$R_y(\tau) = F^{-1}[G_{yy}(w)] \tag{13}$$

these are autocorrelative functions $V_{xx}$ and $V_{yy}$ shown in FIG. 8 corresponding to curves V5 and II shown in FIG. 7.

Curve $V_{xy}$ shown in FIG. 8 is the cross-correlative function which is derived from the following equation by frequency domain processing unit 302:

$$R_{xy}(\tau) = \int_{-\infty}^{\infty} x(t) \cdot y^*(t+\tau)dt \tag{14}$$

therefore, $$R_{xy}(\tau) = F^{-1}[G_{xy}(w)] \tag{15}$$

wherein $R_{xy}(\tau)$ corresponds to $V_{xy}$ shown in FIG. 8.

Referring to FIG. 9, there is shown the space domain processing waveforms of X, Y, Z ECG provided by space domain processing unit 303 shown in FIG. 5 and the vector loops on H, F and LS planes.

Figure 10A:
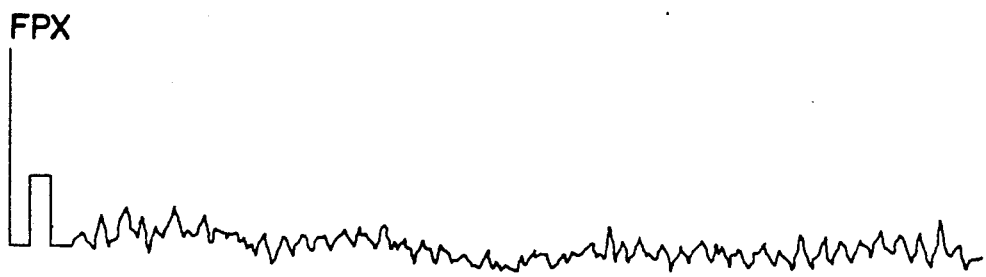
FIGS. 10a-b show the waveforms of EEG time domain processed signals.
Figure 10B:
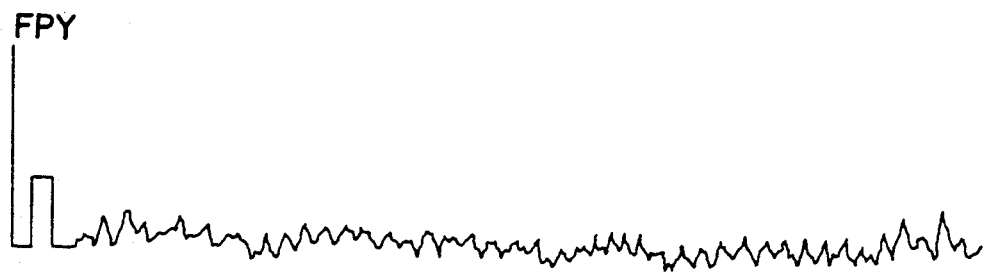

Referring to FIG. 10, there is shown a time domain processing waveforms of conventional EEG provided by the time domain processing unit 301 shown in FIG. 5.

Referring to FIG. 11, there is shown the waveforms provided by the frequency domain processing unit 302 shown in FIG. 5. Curves shown in FIG. 11 are EEG frequency domain processing waveforms obtained by taking FPX and FPY shown in FIG. 10 as X(t) and y(t), respectively, and performing the frequency domain processing thereon. The definition and deduction of each curve is the same as the corresponding one shown in FIG. 8.

Figure 12:
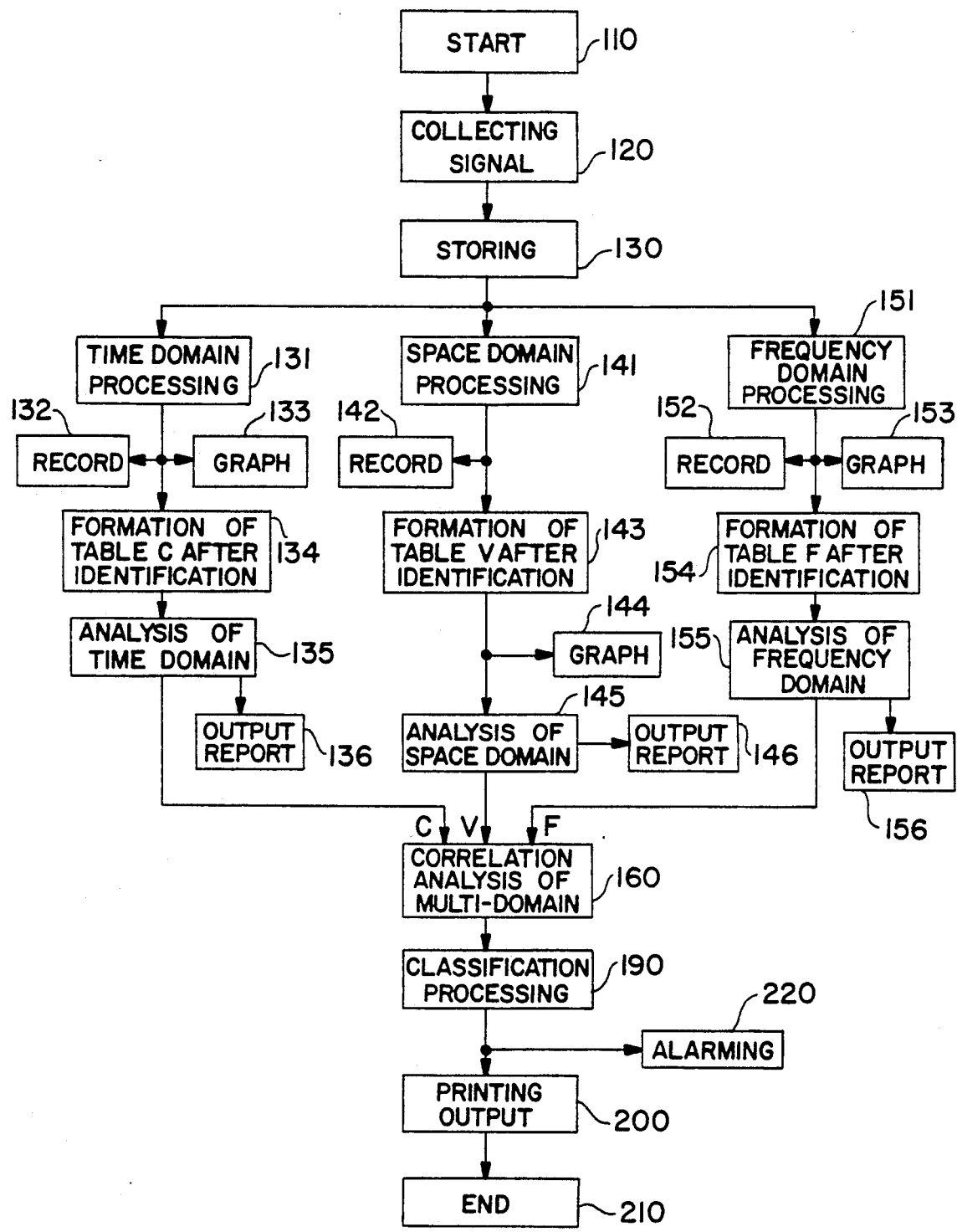
FIG. 12 is the operating flow chart of the apparatus of the present invention.
Figure 14:
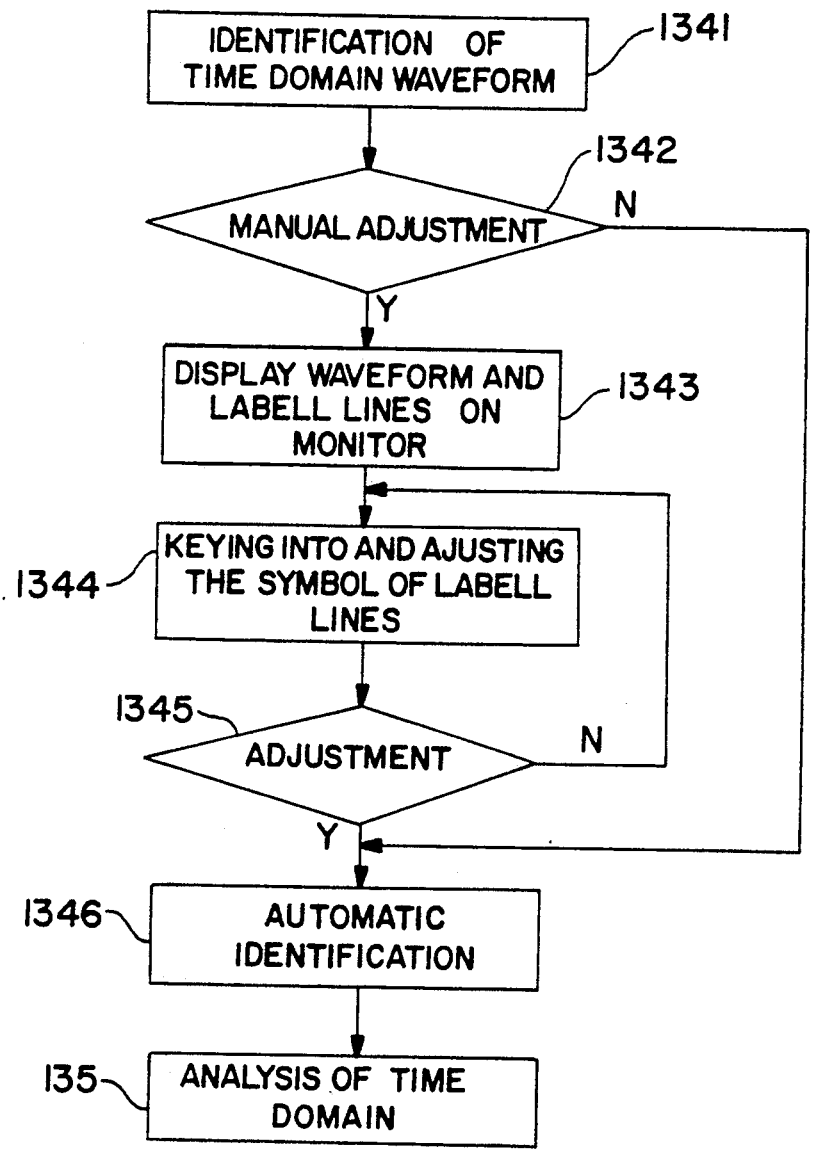
FIG. 14 shows the flow chart of the manual adjustment, taking step 134 shown in FIG. 12 as an example.
Figure 15:
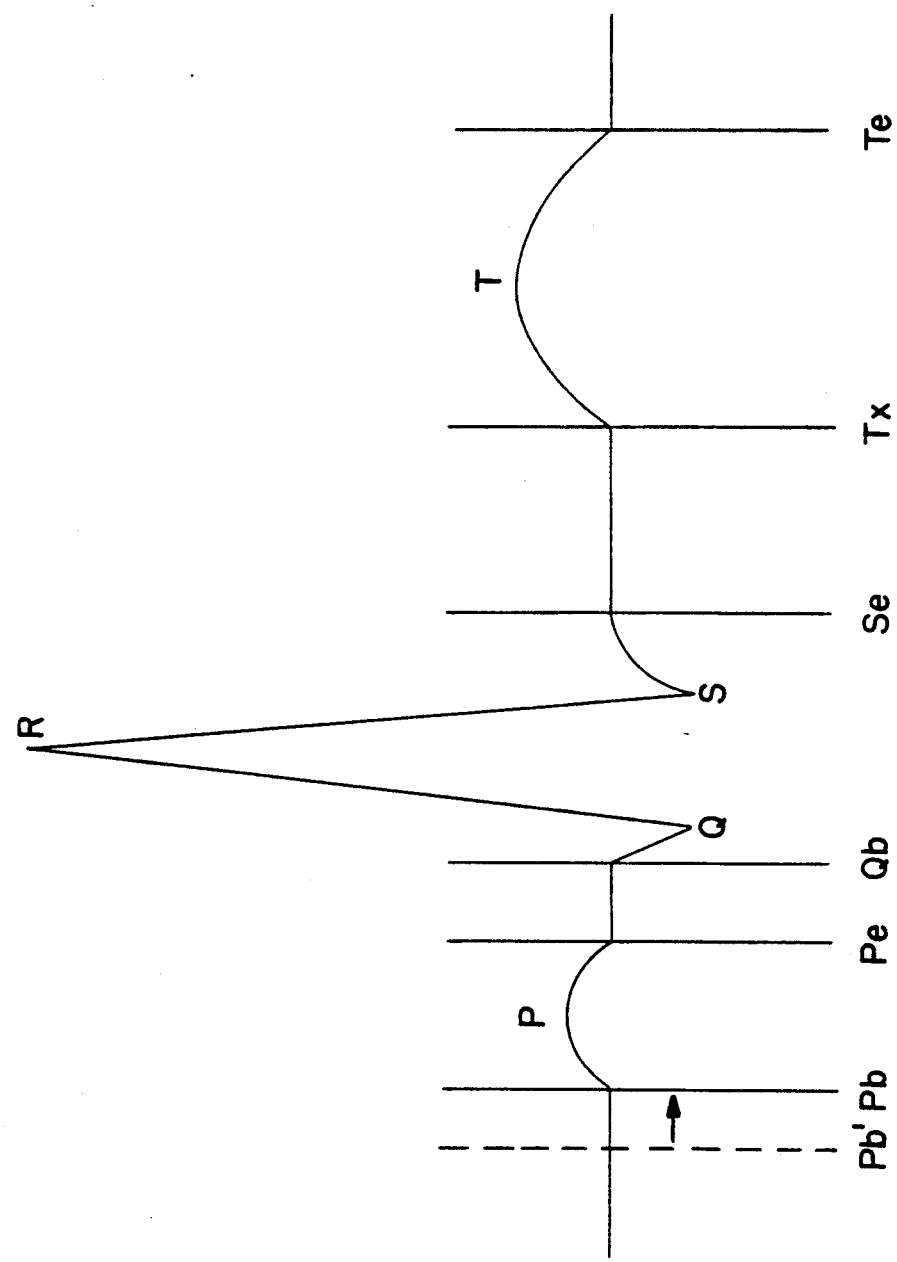
FIG. 15 illustrates the indications used in the manual adjustment process, taking ECG as an example.

Referring to FIG. 12, there is shown an operating flow chart of the apparatus according to the present invention First, the apparatus is initialized and the information about the subject (such as name, sex, age, etc) is fed in via keyboard at step 110, then at step 120, detection is performed on the subject is at different locations of its body by a plurality of electrodes, and at step 130, sampled digital signals are stored for performing time domain, space domain and frequency domain processing at steps 131, 141, and 151, respectively. Next, at steps 132, 142 and 152, data after processing in the time domain, space domain and frequency domain are obtained for storing in external memory. Time and frequency domain waveforms of the bioelectric signals can be plotted based on time domain data and frequency domain data processed at steps 133 and 152 Data processed in three domains are subjected to waveform identification at steps 134, 143 and 154, respectively. All the above-mentioned steps may be executed automatically according to the design of the present invention. (However, manual adjustment is also available if necessary so as to aid the identification for some difficult-to-identify waveforms, its detailed steps are shown in FIGS. 14 and 15 which will be explained later). Accordingly, three parameter tables C (Table 1), V and F are derived, wherein table C contains mainly the amplitudes and durations of the time domain waveforms, such as the amplitudes and durations of P,Q,R,S, and T waves in ECG signals along with heart rate, etc. Table V (Table 3) contains mainly the VCG loop's rotated direction, magnitude, angle, and area e.g. the ratio of areas of a VCG loop in four quadrants, the start and end vectors. Table F (Table 2) contains mainly parameters about the shape and position of frequency domain waveforms, such as peak values and corresponding frequency values of first 4 peaks $g_1-g_4$ of the energy spectrum $G_{xx}$, the values of main peak and negative peak and their frequency locations of the pulse response curve PIH, the amplitude of $r_1$, $r_2$ and $r_3$ and their frequency location of the autocorrelative and cross-correlative functions' curves $V_{xx}$, $V_{yy}$ and $V_{xy}$, the coherent value $f_1$ in coherent function RF whose frequency location corresponds to that of peak $g_1$ in energy spectrum, the maximum height h and its frequency location in the transfer function's curve $H_{xy}$, etc, all of them are shown in FIG. 8. Based on three tables C, V and F, the time, space and frequency domain analysis are performed respectively at steps 135, 145 and 155, and reports of three domain analysis are provided at steps 136, 146 and 156. Then, multi-domain correlative analysis is performed at step 16( (the details of the analysis may refer to the descriptions about FIGS. 13-16). According to the results of this multi-domain correlative analysis, the classifying of diseases is performed at step 190 to provide an analysis report. It is determined on the basis of this report whether to enter the alarming step 220 or not, and finally at step 220 the results are printed. In addition, the VCG graphs may be plotted according to the parameters of of table V at step 44. All curves, parameter tables, analysis results, indicating characters, the starting time and duration of the examination and information about the patient may be quickly printed on the same sheet of paper by, for example, a thermal-printer, then the report may be used by medical staffs.

Figure 13:
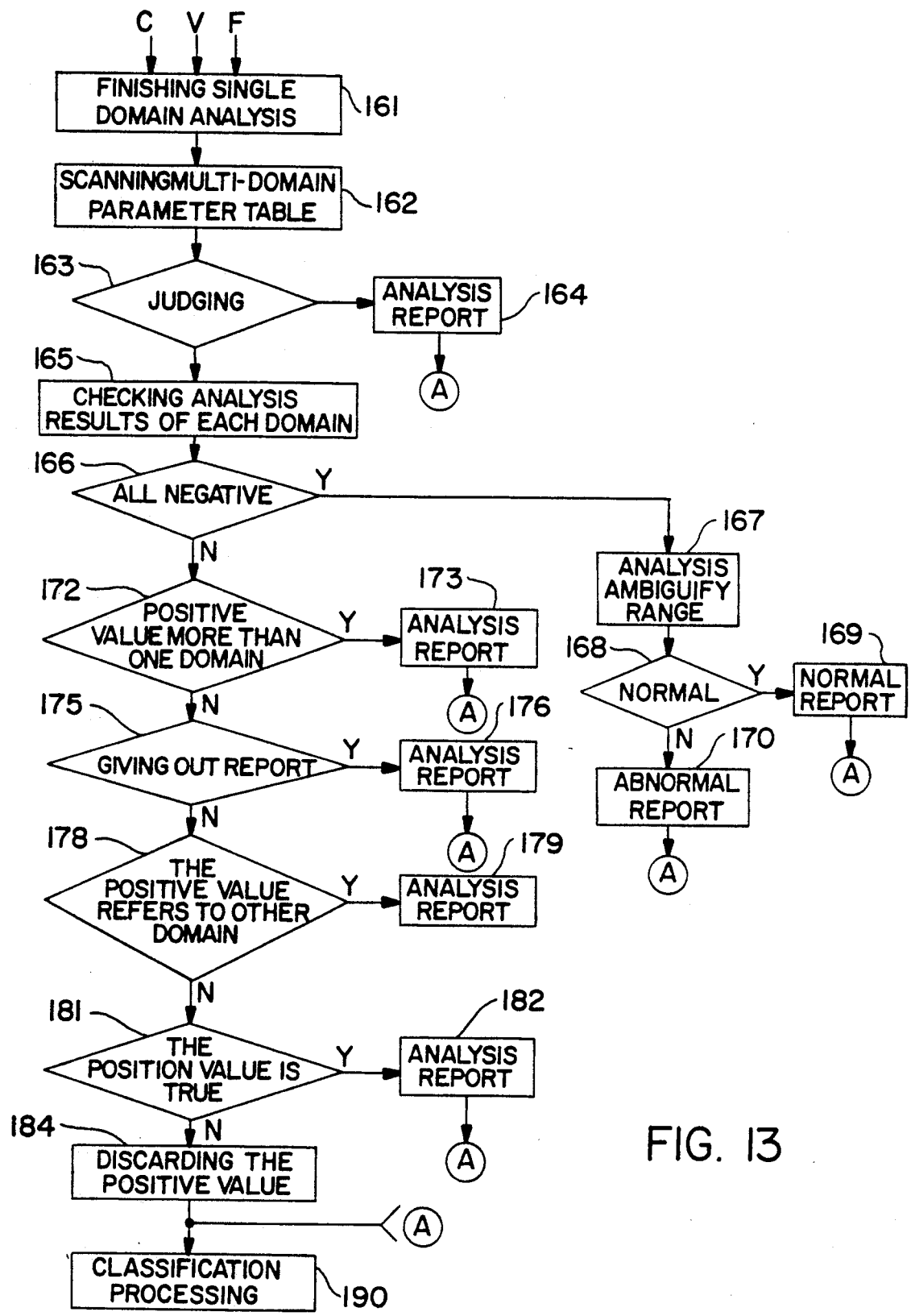
FIG. 13 shows a detailed flow chart of the multi-domain correlative analysis step 160 shown in FIG. 12.

FIG. 13 is a detailed flowchart of the multi domain correlative analysis step 160 in FIG. 12. As shown in FIG. 13, after forming Table C, B, and F (Tables 1, 3, and 2, respectively), it is indicated at step 161 that single domain analysis has been finished, and multi domain parameters are scanned at step 162. Further, the scanned results are compared with predetermined pathological criteria for multi-domain correlative analysis, if they are in conformity with the criteria, the report is given at step 164 to show that the scanned results are within the normal range. On the other hand, if the scanned results are not in the normal range, they will be checked in each single domain at step 165, and if no positive values are found, an ambiguity range analysis will be performed at step 167, its detailed processing may refer to FIG. 16 and its descriptions. By synthetic evaluation of the ambiguity range analysis, the normal report will be given at step 169 if the results meet the requirements of the synthetic evaluation. Otherwise, an abnormal report or a notification will be given at step 170. However, if positive values are found in the single domain analysis results at step 166, the program enters step 172 to determine whether the positive values are in the results of more than one domain. If so, an analysis report is provided at step 173. If it is not the case, the program enters step 175 to determine whether a definite report can be provided on the basis of the present single domain positive values. If so, the report will be given at step 176, otherwise, step 178 is executed to determine whether there are any relationship between the single domain positive values and that of the other two domains. If the relationship exists, a report is given at step 179. Otherwise, the values will be determined whether they are faked or not at step 181, if it is not the case, an indication will be displayed. If it is the case, the faked values will be discarded at step 184. Finally, the determined results are classified into different diseases at step 190 then the program continues. The analysis reports in FIG. 13 all appear in the example of Table 4.

Referring to FIG. 14, there is shown the detailed procedures of steps 134, 143 and 154 of FIG. 12, therein taking step 134 as an example to explain the ECG waveform identification. The waveform identification is started step 1341, and step 1342 is to judge whether manual adjustment is necessary or not. Generally, it is not necessary for normal waveforms and the program enters to step 1346 for automatic identification and table C is formed. For some difficult-to-identify waveforms, the program enters to step 1343 to display the waveforms and label lines for manual adjustment on a CRT as shown in FIG. 15. At step 1344, the operator keys in the symbol of the label lines (such as $P_b$ in FIG. 15) and then move the line to a suitable position. It is decided at step 1345 whether the manual adjustment is finished, if not, it returns to step 1344 for adjusting another line until manual adjustment all finished. Then, at step 1346, table C is formed It should be noticed that since the multi-channel signals are sampled synchroneously, when waveform identification is adjusted on one channel, the waveform positions of the signals of other channels are also determined. Therefore, only one channel of signals selected by operator is displayed on the CRT and segments of the displayed waveform may be enlarged by programming. In this way, the accuracy of the waveform identification for those difficult-to-identify waveforms may be greatly improved.

Referring to FIG. 15, there is shown the start and end positions of P wave, QRS complex and T wave determined by label lines $P_b$, $P_e$, $Q_b$, $S_e$ $T_x$ and $T_e$. Dashed line $P_b'$ is used to show the displacement of line $P_b$ by adjusting.

Figure 16:
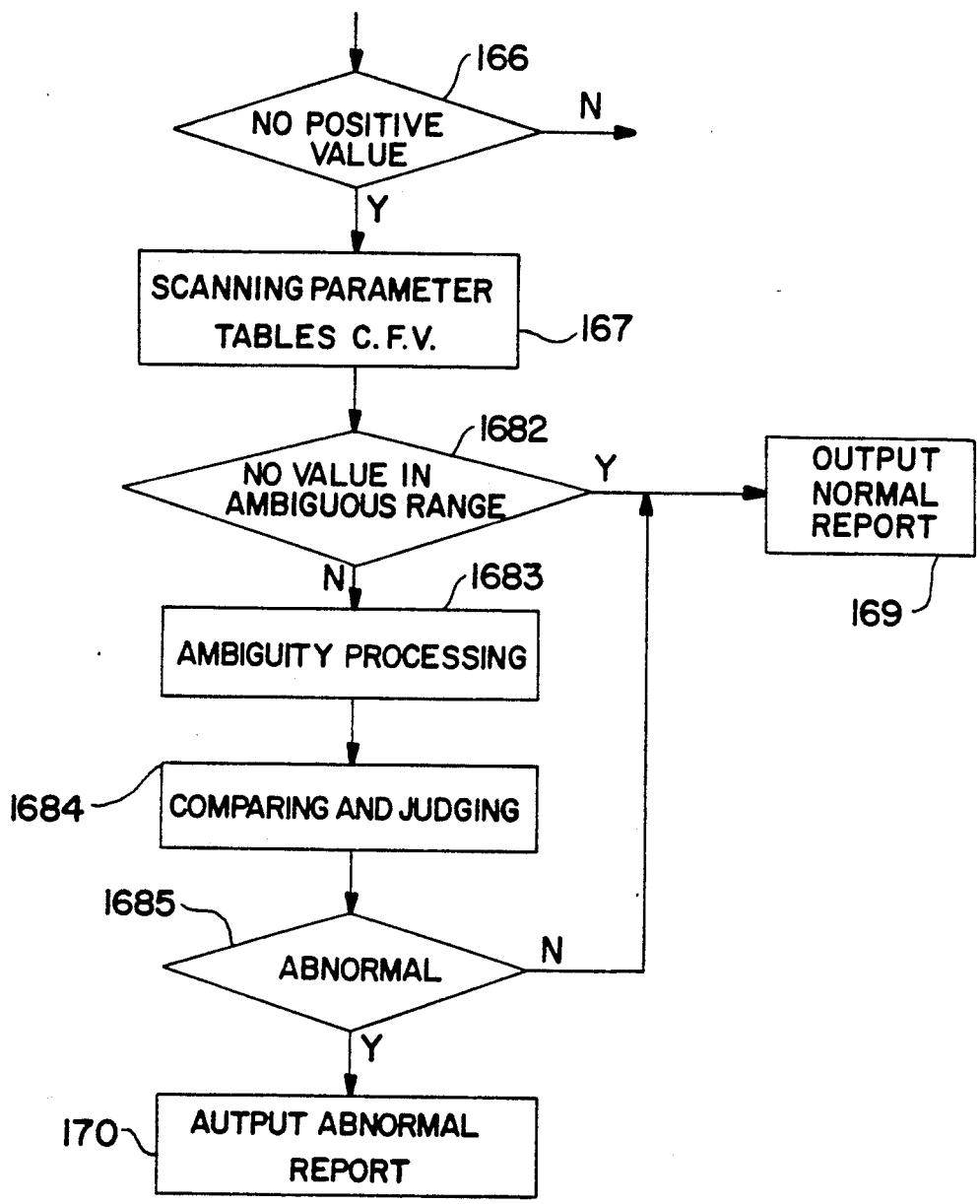
FIG. 16 shows a detailed flow chart for the ambiguous range analysis and scan of steps 167 and 168 shown in FIG. 13.

Referring to FIG. 16, there is shown the detailed flow chart of ambiguous range analysis scanning steps 167 and 168. When no positive value is found in the results of single domain analysis made at step 166 the program enters to step 167 and scans the three tables to determine which parameters are within predetermined ambiguous ranges. It should be pointed out that the values of indexes in each domain may be classified as in the ranges of positive, negative and ambiguous therebetween. The ambiguous ranges are determined on the basis of the experts' experiences and statistical results of many samples of clinical cases. A ambiguous range is defined as a range of a parameter whose value is between the positive and negative values, in this range the status of the patient is ambiguous because it is difficult to differentiate the normal from the slightly abnormal status. For example, if the abnormal value of a parameter is beyond 2.50 mV while the normal one is below 2.40 mV then a value between 2.41 and 2.49 is in the ambiguous range. The situation determined at step 166 as no positive value means that values are in negative range or ambiguous range. If at step 1682 no value in ambiguous range can be found for all parameters of three tables, a normal report will be provided at step 169. If parameters of ambiguous values are found, an ambiguity processing will be carried out to them at step 1683 according to calculation of Euclidean distance of the parameters of ambiguous values, then a multi-domain comparation and analysis of the above caluclated results is performed at step 1684 to determine whether their space distribution is in a predetermined abnormal area, if not, the program returns to step 169 to give a normal report, otherwise, an abnormal report or indication is given at step 170. The reports are found in the example of Table 4.

Figure 17:
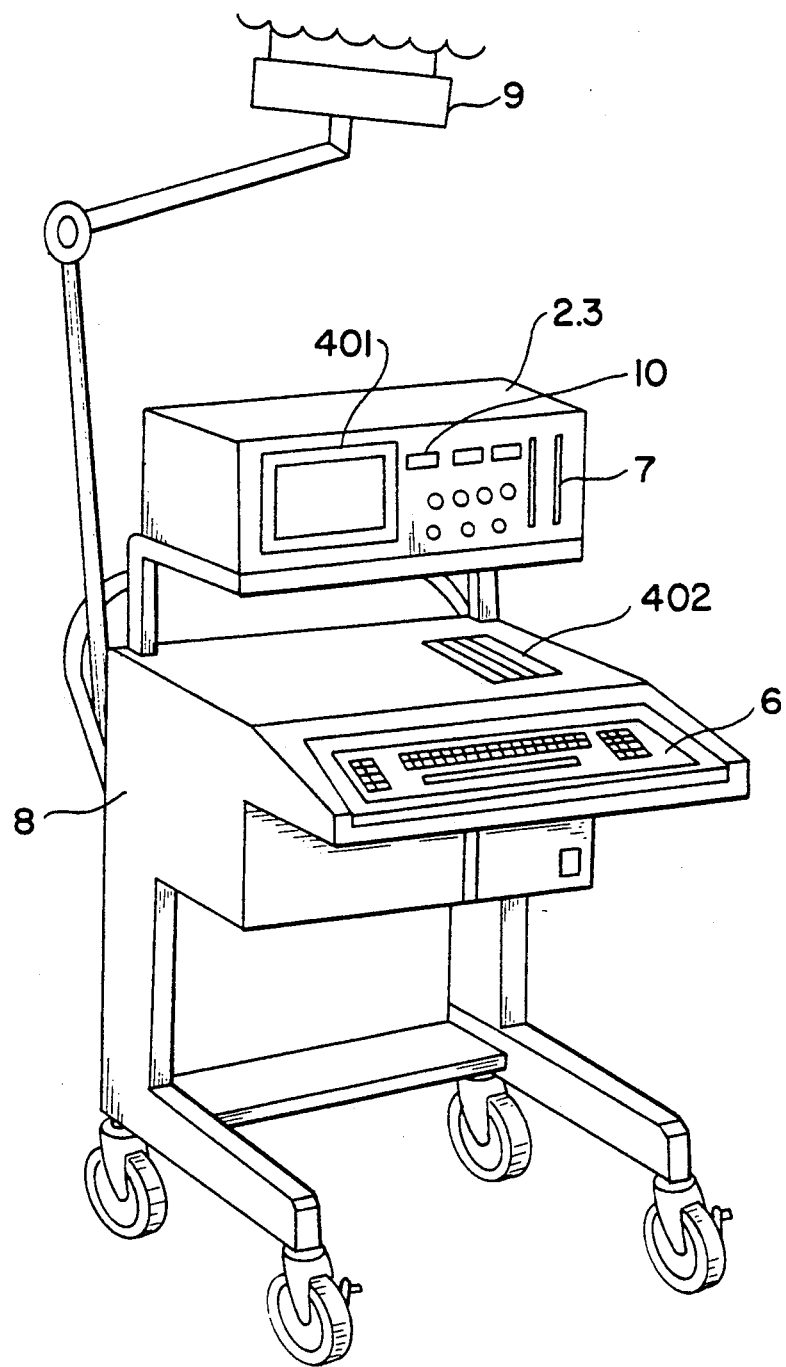
FIG. 17 is an elevation view showing a cart arrangement of an embodiment of the apparatus of the present invention.

Referring to FIG. 17, there is shown the elevation view of a cart arrangement of the apparatus of the present invention. Wherein, numeral 2.3 indicates the main unit which includes electric signal collecting device 2, signal processing device 3, and alarm device 5. Numeral 6 indicates a keyboard, unmeral 7 indicates an external memory and numeral 401 indicates a CRT. The external memory 7 and CRT 401 are assembled with the main unit as a whole. Numeral 402 indicates a high-speed thermosensitive graphic printer numeral 9 indicates a lead supporter, numeral 10 indicates a leads' plug, and numeral 8 indicates cart The arrangement shown in FIG. 17 is convenient for bedside use within hospital and moving from ward to ward. When there is an ambulatory need, the main unit and keyboard may be easily demounted from the cart 8 and engaged into a case by a engagement structure and there is a handle at the back of the main unit for carrying it. An examination can be carried out by such a case and some leads and electrodes. The detected results may be displayed on CRT 401 and stored in external memory 7 for later analysis and acumulation of cases.

Examples of three parameter tables and correlative analysis report may refer to tables 1-4.

It has been, hereinbefore, described the examplary embodiments of the present invention. However, many modifications and rearrangements may be made by those skilled in the art, without departing the spirits and scope of the present invention. Therefore, the scope cf the present invention will by no means be limited to these embodiments and only be defined by the claim attached hereinbelow.

TABLE 1

|     | I   | II  | III  | aVR  | aVL | aVF | V1   | V2  | V3  | V4   | V5   | V6   |
| --- | --- | --- | ---- | ---- | --- | --- | ---- | --- | --- | ---- | ---- | ---- |
| Pa1 | .05 | .08 | .04  | −.08 | .03 | .04 | .02  | .04 | .04 | .05  | .05  | .06  |
| Pa2 | .00 | .00 | .00  | .00  | .00 | .00 | −.09 | .00 | .00 | .00  | .00  | .00  |
| Pd1 | .08 | .09 | .08  | .09  | .08 | .08 | .02  | .08 | .08 | .08  | .08  | .08  |
| Pd2 | .00 | .00 | .00  | .00  | .00 | .00 | .06  | .00 | .00 | .00  | .00  | .00  |
| Oa  | .00 | .00 | −.27 | −.71 | .00 | .00 | −.74 | .00 | .00 | .00  | .00  | .00  |
| Od  | .00 | .00 | .04  | .04  | .00 | .00 | .10  | .00 | .00 | .00  | .00  | .00  |
| Ra  | .85 | .61 | .34  | .06  | .55 | .39 | .00  | .41 | .78 | 1.40 | 1.42 | 1.06 |
| Rd  | .04 | .03 | .07  | .05  | .04 | .03 | .00  | .03 | .03 | .04  | .04  | .04  |

TABLE 1-continued

|     | I    | II   | III | aVR  | aVL  | aVF | V1   | V2    | V3    | V4    | V5   | V6   |
|-----|------|------|-----|------|------|-----|------|-------|-------|-------|------|------|
| Sa  | −.22 | .00  | .00 | .00  | −.29 | .00 | −.74 | −1.50 | −1.44 | −1.24 | −.56 | −.16 |
| Sd  | .06  | .00  | .00 | .00  | .07  | .00 | .10  | .08   | .07   | .07   | .07  | .05  |
| STD | .00  | .00  | .00 | .00  | .00  | .00 | .00  | .00   | .00   | .00   | .00  | .00  |
| STE | .00  | .00  | .00 | .00  | .00  | .00 | .00  | .00   | .00   | .00   | .00  | .00  |
| Ta1 | .10  | .12  | .00 | −.10 | .07  | .08 | .05  | .24   | .24   | .19   | .09  | .09  |
| Ta2 | .00  | .00  | .03 | .00  | .00  | .00 | .00  | .00   | .00   | .00   | .00  | .00  |
| P-R | .14  | .15  | .14 | .14  | .14  | .16 | .14  | .14   | .14   | .14   | .14  | .14  |
| Q-T | .38  | .37  | .38 | .37  | .38  | .36 | .37  | .39   | .39   | .39   | .38  | .38  |
| QRS | .10  | .06  | .11 | .09  | .11  | .06 | .20  | .11   | .10   | .11   | .11  | .09  |
| R1a | .00  | .14  | .00 | .00  | .00  | .25 | .00  | .00   | .00   | .00   | .00  | .00  |
| R1d | .00  | .03  | .00 | .00  | .00  | .03 | .00  | .00   | .00   | .00   | .00  | .00  |
| Tag | .00  | .00  | .00 | .00  | .00  | .00 | 73.0 | .00   | .04   | .00   | .00  | .00  |

TABLE 2

| GXX | GYY | ½ | HG | HN | ½N | TU | 5/10 |
|-----|-----|---|----|----|----|----|------|
| X   | +   | − | −  | −  | −  | −  | −    |
| Y   | +   | − | −  | −  | −  | −  | −    |
| PIH | RF  | PV | M1 | M2 | M3 | CP | CT |
|     | −   | −  | −  | −  | −  | −  | −  |
| QXY | VXY | D  | W  | D+W | RV | RD | APT |
|     | +   |    |    |     |    |    |     |
| VXY | VYY | RH | RL | FPX | FPY | − | |
|     |     | −  | −  |     |     |   | |

PARAMETER TABLE

| GXX   | GYY  | 1    | 2    | 3    | 4    | 5     | 6    |
|-------|------|------|------|------|------|-------|------|
| XA    |      | 1.2  | 6.1  | 8.7  | 5.0  | 14.2  | 12.1 |
| YA    |      | 1.2  | 2.3  | 3.6  | 4.0  | 3.1   | 4.1  |
| VXX   | VYY  | R1X  | R2X  | R3X  | R1Y  | R2Y   | R3Y  |
| A     |      | 11.96| 7.50 | 4.02 | 1.77 | 1.02  | 0.90 |
| PIH   |      | 1    | 2    | 3    | 4    | 5     | 6    |
| A     |      | −0.1 | −6.78| 19.03| 1.50 | 4.20  | −1.02|

TABLE 3

ROTATED DIRECTION

|     | QRS     | T       | P       |
|-----|---------|---------|---------|
| F:  | CLOCK   | COUNTER | CLOCK   |
| H:  | COUNTER | COUNTER | CLOCK   |
| LS: | COUNTER | CLOCK   | COUNTER |

MAGNITUD/ANGLE OF VECTORS ON QRS LOOP (STEP 10 MS)

|     |      | 10 ms  | 20 ms | 30 ms  | 40 ms |
|-----|------|--------|-------|--------|-------|
| F:  | (MV) | .178   | .684  | 1.222  | .649  |
|     | (A)  | 358.87 | 8.34  | 20.00  | 45.00 |
| H:  | (MV) | .161   | .690  | 1.204  | .820  |
|     | (A)  | 33.89  | 7.58  | 350.87 | 305.98|
| LS: | (MV) | .148   | .321  | .961   | .943  |
|     | (A)  | 150.43 | 75.48 | 42.70  | 30.17 |

AREA OF QRS LOOP (%)

|     | S1/S  | S2/S  | S3/S  | S4/S  | R/L  | U/D   | PS    |
|-----|-------|-------|-------|-------|------|-------|-------|
| F:  | 78.92 | 19.21 | .00   | 1.75  | 4.19 | .02   | .0001 |
| H:  | 8.90  | .00   | 22.77 | 68.30 | 3.39 | 10.23 | .0409 |
| LS: | 82.33 | 11.76 | 5.88  | .00   | 4.67 | .06   | .0001 |

PLANAR MAXIMUM VECTORS

|     | T |  | QRS |  | QRS-T |
|     | (MV) | ANGLE | (MV) | ANGLE | ANGLE |
|-----|------|--------|-------|---------|----------|
| F:  | .158 | 60.030 | 1.222 | 13.251  | 46.779   |
| H:  | .086 | .000   | 1.206 | 345.987 | −345.987 |
| LS: | .139 | 79.254 | .916  | 27.348  | 51.906   |

PROJECTIONS OF PLANAR MAXIMUM VECTORS

|     | X    | Y   | Z    |
|-----|------|-----|------|
| F:  | 1.19 | .28 | .00  |
| H:  | 1.17 | .00 | −.29 |
| LS: | .00  | .42 | .81  |

TABLE 4

| NO: 953   | NAME: HUANG LAN MING | SEX: FEMALE  | AGE: 55 |
|-----------|---------------------|--------------|---------|
| HR: 73.00 | AXSIS: 7.00         | QRS: 0.10    |         |
| P-R: 0.15 | FCGV: 8.0           | VCC: 1.25 mv |         |

COMPREHESIVE DIAGNOSIS REPORT:
NORMAL SINUS RHYTHM.
MYOCARDIAL ISCHEMIA.
ECG ANALYSIS:
SUSPECTED ABNORMAL Q WAVE:       V1
LOW AMPLITUDE OF T:              V5, V6. Tv 1.2 > Tv 5.6.
FCG ANALYSIS:
ABNORMAL +
MYOCARDIAL ISCHEMIA.
ABNORMAL TERM:                   ½X, ½Y, D, FPT.
VCG ANALYSIS:
POSTERIOR DEVIATION OF THE QRSh LOOP.
A SMALL T LOOP AND QRS/T > 6 IN H PLANE.
A LARGE QRS-T ANGLE IN F PLANE.

---

What is claimed is:

1. An apparatus for detecting and processing electrocardiogram (ECG) signals, comprising:

a plurality of detecting electrodes;

detecting means, operatively connected to said plurality of detecting electrodes, for simultaneously detecting ECG signals on multiple leads and for amplifying the multi-lead ECG signals to provide multi-lead amplified ECG outputs;

multi-channel A/D converter means, operatively connected to said detecting means, for converting synchronously amplified ECG outputs of each lead into multi-channel digital data;

buffer memory means, operatively connected to said A/D converter means, for storing said synchronized multi-channel digital data;

processing means or processing the stored multi-channel digital data corresponding to the detected ECG signals;

said processing means including frequency domain processing means for fetching the stored multichannel digital data from two selected leads corresponding to a plurality of heart beats from said buffer memory means and for performing a fast Fourier transform on each individual lead of the fetched data;

said frequency domain processing means calculating an energy spectrum for each lead, a cross-energy spectrum and transfer function curves for said two selected leads; and output means, operatively connected to said processing means, for providing waveforms of the calculated results of said frequency domain processing means as an output.

2. The apparatus for detecting and processing ECG signals as claimed in claim 1, wherein said frequency domain processing means further calculates a coherent function curve of said two selected leads and said output means provides said coherent function wave as an output.

3. The apparatus for detecting and processing ECG signals as claimed in claim 1, wherein said frequency domain processing means further calculates a pulse response curve of said two selected leads and said output means provides said pulse response curve as output.

4. The apparatus for detecting and processing ECG signals as claimed in claim 1, wherein said frequency domain processing means further calculates auto correlative function curve of each lead and cross-correlative function curve of said two selected leads and said output means provides the curves as output.

5. The apparatus for detecting and processing ECG signals as claimed in claim 1, wherein said processing means further includes time domain processing means for fetching each lead of said stored multi-channel digital data corresponding to a plurality of heart beats from said buffer memory means and for producing ECG waveform data corresponding to the fetched data; and said output means outputting ECG waveforms corresponding to said ECG waveform data.

6. The apparatus for detecting and processing ECG signals as claimed in claim 1, wherein said detecting means detects at least three leads of said ECG signals;

said processing means further including time domain processing means for fetching each lead of the stored multi-channel digital data corresponding to a plurality of heart beats from said buffer memory means and for producing ECG waveform data corresponding to the fetched data;

said output means outputting ECG waveforms corresponding to said ECG waveform data;

said frequency domain processing means further calculating at least one curve from a group of curves, a pulse response curve, an auto-correlative function curve, and a cross-correlative function curve;

said output means outputting waveforms corresponding to the calculated curves;

said processing means further including space domain processing means for fetching three selected leads of the stored multi-channel digital data from said buffer memory means corresponding to a complete period of one heart beat to form front plane vector loops, horizontal plane vector loops, and left side plane vector loops; and said output means outputting said vector loops.

7. The apparatus for detecting and processing ECG signals as claimed in claim 6, wherein said processing means further includes:

time domain waveform identification means, operatively connected to said time domain processing means, for identifying said ECG waveforms data provided by said time domain processing means and for calculating amplitude and width of each set of waveform data;

frequency domain waveform identification means, operatively connected to said frequency domain processing means, for identifying said waveforms provided by said frequency domain processing means and for calculating at least one parameter from a group of parameters, said group of parameters including peak values and corresponding frequency values of first four peaks from said energy spectrum, values of a main peak and a negative peak from said pulse response curve and corresponding frequency locations of said main and negative peaks from said pulse response curve, peak values and corresponding frequency locations of said peak values from said auto-correlative function and cross-correlative function curves, a coherent value from said coherent function curve wherein a frequency location of said coherent value corresponds to a first peak in said energy spectrum, and maximum height and corresponding frequency location of said maximum height from said transfer function curve; and space domain waveform identification means, operatively connected to said space domain processing means, for identifying shapes and locations of said vector loops provided by said space domain processing means and for calculating parameters corresponding to area, angle and rotated direction of said vector loops;

said time domain waveform identification means, said frequency domain waveform identification means, and said space domain waveform identification means forming three tables of parameters; and wherein said output means outputting said three tables of parameters.

8. The apparatus as claimed in claim 7, wherein said processing further includes computer means for synchronously sampling said multi-lead amplified outputs provided by said detecting means at a frequency in the range of 500 Hz to 2,500 Hz and for performing at least one calculation in time domain, frequency domain, and space domain on the sampled signals to produce multi-domain outputs.

9. A method for detecting and processing electrocardiogram (ECG) signals, comprising the steps of:
(a) detecting simultaneously the ECG signals from multi-leads located at different locations on a living body via a plurality of detecting electrodes;
(b) amplifying the detected signals of said step (a) by a multi-channel amplifying circuit;
(c) digitizing synchronously the multi-channel amplified signals of step (b);
(d) storing the synchronized digital data of said step (c) in a buffer memory;
(e) fetching two selected leads of the stored data of said step (d) from the buffer memory;
(f) performing a fast Fourier transform on each individual lead of the fetched data of said step (e);
(g) calculating an energy spectrum for each selected individual lead;
(h) calculating a cross-energy spectrum and transfer function curves for the two selected leads; and (i) displaying waveforms of the cross-energy spectrum calculation and transfer function curves of said step (h).

10. The method for detecting and processing ECG signals as claimed in claim 9, further comprising the steps of:
    (j) calculating a coherent function curve of the two selected leads; and
    (k) displaying waveforms of the coherent function curve of said step (j).

11. The method for detecting and processing ECG signals as claimed in claim 9, further comprising the steps of:
    (j) calculating a pulse response curve of the two selected leads; and
    (k) displaying waveforms of the pulse response curve calculation of said step (j).

12. The method for detecting and processing ECG signals as claimed in claim 9, further comprising the steps of:
    (j) calculating an auto-correlative function curve for each individual lead and cross-correlative function curve for the two selected leads; and
    (i) displaying waveforms of the auto-correlative function curve and the cross-correlative function curve of said step (j).

13. The method for detecting and processing ECG signals as claimed in claim 9, further comprising the steps of:
    (j) fetching each individual lead of the stored data of said step (d) from the buffer memory;
    (k) producing time domain waveforms of the fetched data of said step (j); and
    (l) displaying the time domain waveforms of said step (k).

14. The method for detecting and processing bioelectric signals as claimed in claim 9, wherein said detecting step (a) detects at least three leads of ECG signals, X, Y, and Z, and further comprising the steps of:
    (j) fetching each individual lead of stored ECG data of said step (d) from the buffer memory:
    (k) producing ECG waveforms from the fetched data of said step (j);
    (l) displaying the ECG waveforms of said step (k);
    (m) calculating at least one curve from a group of curves including a coherent function curve, a pulse response curve, an auto-correlative function curve, and a cross-correlative function curve;
    (n) displaying the curve or curves calculated in said step (m) in a waveform manner;
    (o) fetching three leads of the stored ECG data of said step (d), corresponding to the signals X, Y and Z, from the buffer memory;
    (p) forming front plane vector loops from the signals X and Y;
    (q) forming horizontal plane vector loops from the signals X and Z;
    (r) forming left side plane vector loops from the signals Y amd Z; and
    (s) displaying the vector loops of said steps (p), (q) and (r).

15. The method for detecting and porcessing ECG signals as claimed in claim 14, further comprising the steps of:
    (t) identifying the ECG waveforms provided by said step (k);
    (u) calculating an amplitude and width of each wave identified in said step (t);
    (v) identifying the curve or curves calculated by said step (m);
    (w) calculating at least one parameter from a group of parameters including peak values and corresponding frequency values of first four peads g1, g2, g3, and g4, from the energy spectrum values, a main peak and a negative peak and corresponding frequency locations from the pulse response curve, peak values and corresponding frequency locations from the auto-correlative function and cross-correlative function curves, a coherent value from the coherent function curve, wherein a frequency location of the coherent value corresponds to the pead g1 of the energy spectrum, and maximum height and corresponding frequency location from the transfer function curve;
    (x) identifying shapes and locations of the vector loops formed by said steps (p), (q) and (r);
    (y) calculating parameters of area, angle and rotated direction of the vector loops;
    (z) producing three tables of the parameters calculated by said steps (u), (w) and (y); and
    (aa) displaying the tables of parameters produced in said step (z).

16. An apparatus for detecting and processing ECG signals, comprising:
    a plurality of detecting electrodes including 12 Wilson's leads and 3 Frank's leads;
    detecting means, operatively connected to said detecting electrodes, for simultaneously detecting 12 Wilson's leads and 3 Frank's leads of ECG signals and for amplifying the detected signals to provide 15 leads of amplified ECG output;
    multi-channel A/D converter means, operatively connected to said detecting means, for synchronously converting said 15 leads of amplified ECG outpots into 15 channels of digital data;
    buffer memory means, operatively connected to said multi-channel A/D converter means, for storing the synchronized 15-channel of digital data; processing means, operatively connected to said buffer memory means, for processing the synchronized 15-channels of digital data;
    said processing means including,
        time domain processing means, operatively connected to said buffer memory means, for fetching at least the stored digital data of each of the 12 Wilson's leads corresponding to a plurality of heart beats and for forming ECG waveforms corresponding to each individual lead of fetched data,
        frequency domain processing means, operatively connected to said buffer processing means, for fetching the stored digital data of leads II and V5 of the 12 Wilson's leads corresponding to a plurality of heart beats and for performing a fast Fourier transform on each individual lead of the fetched data,
        said frequency domain processing means calculating at least one curve form a group of curves including an energy spectrum curve for each lead, cross-energy spectrum curve for the two selected leads, transfer function curves, a coherent function curve, a pulse respnise curve, and auto-correlative function curve, and a cross-correlative function curve,
        space domain processing means, operatively connected to said buffer memory means, for fetching three Frank's leads, corresponding to signals X, Y, and Z, of the stored digital data corresponding to a complete period of one heart beat and for producing front plane vector loops from said signals X and Y, horizontal plane vector loops from said signals X and Z, and left side plane vector loops from said signals Y and Z, time domain waveform identification means, operatively connected to said time domain processing means, for identifying said ECG waveforms and for calculating an amplitude and width of each waveform, frequency domaim waveform identification means, operatively connected to said frequency domain processing means, for identifying said curves and for calculating at least one parameter from a group of parameters including peak values and corresponding frequency values of first four peaks, g1, g2, g3, and g4, from said energy spectrum curve, a main peak and a negative peak and corresponding frequency locations from said pulse response curve, peak values and corresponding frequency locations from said auto-correlative function and cross-correlative function curves, coherent value from said energy spectrum, and maximum height and corresponding frequency location from said transfer function curve, space domain waveform identification means, operatively connected to said space domain processing means, for identifying sghapes and colations of said vector loops and for calculating parameters corresponding to the area, angle and rotated direction of said vector loops; and output menas, operatively connected to said processing means, for displaying said ECG waveforms, said curves produced by said frequency domain means according to signals of leads II and V5, said vector loops of the three planes corresponding to said signals of X, Y, and Z, and three parameter tables calculated from the time domain waveforms, frequency domain curves, and space domain vector loops, respectively.

* * * * *